United States Patent

Foulon et al.

[11] Patent Number: 5,994,350
[45] Date of Patent: Nov. 30, 1999

[54] 3-SPIRO-INDOLIN-2-ONE DERIVATIVES AS VASOPRESSIN AND/OR OXYTOCIN RECEPTOR LIGANDS

[75] Inventors: Loïc Foulon, Pinsaguel; Georges Garcia, Frontignan; Claudine Serradeil-Le Gal, Escalquens; Gérard Valette, Lacroix-Falgarde, all of France

[73] Assignee: Sanofi-Synthelabo, Paris, France

[21] Appl. No.: 09/051,900

[22] PCT Filed: Oct. 24, 1996

[86] PCT No.: PCT/FR96/01666

§ 371 Date: Apr. 17, 1998

§ 102(e) Date: Apr. 17, 1998

[87] PCT Pub. No.: WO97/15556

PCT Pub. Date: May 1, 1997

[30] Foreign Application Priority Data

Oct. 24, 1995 [FR] France ................... 95 12533

[51] Int. Cl.⁶ ............... A61K 31/40; A61K 31/535; C07D 209/06; C07D 413/12
[52] U.S. Cl. ............. 514/232.8; 514/409; 544/6; 544/70; 544/230; 546/15; 348/411
[58] Field of Search .............. 544/70, 230; 546/15; 548/411; 514/232.8

[56] References Cited

U.S. PATENT DOCUMENTS

| 5,618,833 | 4/1997 | Foulon et al. |
| 5,663,431 | 9/1997 | Di Malta et al. |
| 5,686,624 | 11/1997 | Di Malta et al. |
| 5,696,145 | 12/1997 | Foulon et al. |
| 5,726,322 | 3/1998 | Di Malta et al. |

FOREIGN PATENT DOCUMENTS

| 636608 | 2/1995 | European Pat. Off. |
| 636609 | 2/1995 | European Pat. Off. |
| WO93/15051 | 8/1993 | WIPO |

Primary Examiner—Robert W. Ramsuer
Attorney, Agent, or Firm—Michael D. Alexander

[57] ABSTRACT

The subject of the invention is indolin-2-one derivatives of formula:

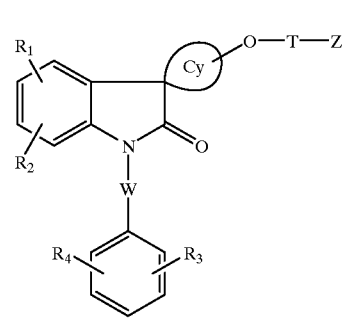

in which:

W represents a —$CH_2$— or —$SO_2$— group;

Cy forms, with the carbon to which it is bonded, a non-aromatic, saturated or unsaturated $C_3$–$C_{12}$ hydrocarbon ring which is optionally condensed or substituted by one or a number of ($C_1$–$C_7$)alkyl groups, it being possible for the said groups to substitute the same carbon atom one or a number of times, or by a $C_3$–$C_6$ spirocycloalkyl;

T represents a ($C_1$–$C_4$)alkylene which is optionally interrupted by a ($C_3$–$C_6$)cycloalkylene, the said alkylenes optionally being substituted one or a number of times on the same carbon atom by a ($C_1$–$C_3$)alkyl; or alternatively T represents a direct bond;

Z represents in particular an amino group;

$R_1$ and $R_2$, as well as $R_3$ and $R_4$, are either hydrogen or substituents, such as, for example, a halogen, an alkyl, and the like.

23 Claims, No Drawings

3-SPIRO-INDOLIN-2-ONE DERIVATIVES AS VASOPRESSIN AND/OR OXYTOCIN RECEPTOR LIGANDS

This application if a 371 of PCT/FR96/01666 filed Oct. 24, 1996.

The subject of the present invention is new indolin-2-one derivatives and a process for their preparation. These new derivatives possess an affinity for vasopressin and/or oxytocin receptors and can thus constitute active principles of pharmaceutical compositions.

Vasopressin is a hormone known for its antidiuretic effect and its effect in the regulation of arterial pressure. It stimulates a number of receptor types: $V_1$ ($V_{1a}$, $V_{1b}$ or $V_3$), $V_2$. These receptors are located in the liver, the vessels (coronary, renal or cerebral), the platelets, the kidney, the uterus, the suprarenal glands, the central nervous system or the hypophysis. Oxytocin has a peptide structure similar to that of vasopressin. The oxytocin receptors are also found on the smooth muscle of the uterus; they are also found on the myoepithelial cells of the mammary gland, in the central nervous system and in the kidney. The localization of the different receptors is described in: Jard S. et al., "Vasopressin and Oxytocin Receptors: an Overview in Progress" in Endocrinology, Imura H. and Shizurne K., published by Experta Medica, Amsterdam, 1988, 1183–1188 and in the following articles: Presse Médicale, 1987, 16 (10), 481–485, J. Lab. Clin. Med., 1989, 114 (6), 617–632 and Pharmacol. Rev., 1991, 43 (1), 73–108. Vasopressin thus exerts hormonal, cardiovascular, hepatic, renal, antidiuretic and aggregant effects and effects on the central and peripheral nervous systems, on the uterine and intestinal areas and on the ocular and pulmonary system. Oxytocin is involved in parturition, lactation and sexual behaviour.

Antagonists of the $V_2$ receptors of vasopressin (also known as "AVP-2-antagonists" or "$V_2$ antagonists") can be recommended as powerful aquaretics which act specifically on renal reabsorption of water without resulting in losses of electrolytes ($Na^+$ or $K^+$), as induced by the diuretics conventionally used clinically, such as furosemide or hydrochlorothiazide. The latter result, after prolonged treatment, in hypokalaemias and hyponatraemias.

The first antagonist of the $V_2$ receptors of arginine-vasopressin (hereinafter known as AVP), OPC-31260, is currently in the course of clinical development Comparison of the effects of OPC31260 with conventional diuretics, such as furosemide, demonstrates that both in animals (Yoshitaka Y. et al., Br. J. Pharmacol., 1992, 105, 787–791) and in man (Akihiro O. et al., J. Clin. Invest, 1993, 92, 2653–2659, and Akihiro O. et al., J. Pharmacol. Exp. Ther., 1995, 272, 546–551) such a compound selectively promotes aqueous diuresis and has no effect, or very little effect at high doses, on the excretion of ions, Indolin-2-one derivatives have been described in the literature. Mention may be made, by way of example, of Patent ZA 830952, which describes derivatives which are useful as antihypertensives which inhibit the converting enzyme, or Patent FR 1,509,373, which describes diuretic compounds which have an effect on potassium excretion.

A number of patent applications or patents also describe series of non-peptide compounds having an affinity for vasopressin and/or oxytocin receptors. This is the case, for example, with EP 382,185, which describes carbostyryl derivatives, which are vasopressin antagonists, which are useful as vasodilators, hypotensives, diuretics and platelet antiaggregants; EP 444,945, which describes spiropiperidine derivatives which are useful in particular in dysmenorrhoea; EP 514,667, which describes benzazepine derivatives which are useful in particular in disorders of renal function, in hyponatraemia, diabetes or alternatively in the treatment and the prophylaxis of hypertension and in the inhibition of platelet aggregation: JP 03127732 which described indole derivatives as vasopressin antagonists.

Benzyl or sulphonylindoline derivatives and indole derivatives have also been described as vasopressin antagonists. To this end, mention may be made of the documents EP 469,984, EP 526,348, EP 636,608, EP 636,609, WO 93/15051 and WO 95/18105 but these docu-ments do not describe compounds which are selectively active with respect to the AVP-2 receptor.

It has now been found that certain indolinones exhibit an excellent affinity with respect to vasopressin and/or oxytocin receptors. These new indolin-2-ones are powerful and selective AVP-2-antagonists. Moreover, taking into account their structure and in particular the presence of various polar functional groups, in particular salifiable functional groups, these molecules are readily dispersible and/or soluble in water, which confers on them an improved pharmacological activity, and also make possible the ready preparation of injectable pharmaceutical dosage forms.

Thus, according to one of its aspects, the present invention relates to new indolin-2-ones corresponding to the formula:

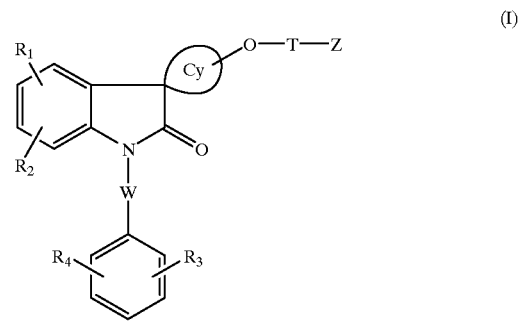

in which:

$R_1$ and $R_2$ each independently represent a hydrogen; a hydroxyl; a halogen; a ($C_1$–$C_7$)alkyl; a ($C_1$–$C_7$)polyfluoroalky; a ($C_1$–$C_7$)alkoxy; a ($C_1$–$C_7$)alkylthio; a ($C_1$–$C_7$)polyfluoroalkoxy; a ($C_3$–$C_7$)-cycloalkyloxy; a ($C_3$–$C_7$) cycloalkylthio; a cycloalkylmethoxy or a cycloalkyl-methylthio in which the cycloalkyl is $C_3$–$C_7$; a phenoxy; a benzyloxy; a nitro; or a cyano;

$R_3$ and $R_4$, independently of one another, substitute the phenyl group one or a number of times and each independently represent a hydrogen; a halogen; a $(C_1-C_7)$ alkyl; a $(C_2-C_7)$alkenyl; a $(C_{1-C_7})$ polyhaloalkyl; a phenyl or a benzyl; a cyano; a nitro; an —$NR_5R_6$ group; a hydroxy-amino; a hydroxyl; an $OR_7$ group; an $SR_7$ group; a —$COOR_8$ group, a —$CONR_9R_{10}$ group; or a —$CSNR_9R_{10}$ group, at least one of the $R_3$ and $R_4$ radicals being other than hydrogen;

$R_5$ and $R_6$ each independently represent a hydrogen; a $(C_1-C_7)$alkyl; a $(C_2-C_7)$alkenyl; a phenyl; a benzyl; a $(C_1-C_7)$alkylcarbonyl; a $(C_1-C_7)$alkylthiocarbonyl; a $(C_3-C_7)$cycloalkylcarbonyl; a $(C_3-C_7)$cycloalkylthiocarbonyl; a benzoyl; a thienylcarbonyl; a furylcarbonyl; a $(C_1-C_7)$alkyloxycarbonyl; a phenoxycarbonyl; a benzyloxy-carbonyl; a carbamoyl or a thiocarbamoyl which is unsubstituted or substituted by $R_9$ and $R_{10}$ or alternatively $R_5$ and $R_6$ form, with the nitrogen atom to which they are bonded, a heterocyclic group chosen from the pyrrolidine, pyrroline, pyrrole, indoline, indole and piperidine groups;

$R_7$ represents a $(C_{1-C_7})$alkyl; a $(C_2-C_7)$alkenyl; a phenyl; a benzyl; a $(C_3-C_7)$cycloalkyl; a $(C_1-C_7)$polyfluoroalkyl; a formyl; a $(C_1-C_7)$alkylcarbonyl; a benzoyl; or a benzylcarbonyl;

$R_8$ represents a hydrogen; a $(C_1-C_7)$alkyl; a phenyl; or a benzyl;

$R_9$ and $R_{10}$ each independently represent hydrogen; a $(C_1-C_7)$alkyl; a $(C_1-C_7)$polyfluoroalkyl; a $(C_2-C_7)$ alkenyl; a $(C_3-C_7)$cycloalkyl, optionally substituted by a hydroxy $(C_1-C_4)$alkyl; a pyridyl; a phenyl; a thienyl; a furyl; or alternatively $R_9$ and $R_{10}$ form, with the nitrogen atom to which they are bonded, a heterocyclic group chosen from the pyrrolidine, piperidine or piperazine groups, which are unsubstituted or substituted by $(C_1-C_4)$alkyls and the $(C_4-C_7)$azacycloalkyl groups;

W represents a —$CH_2$— or —$SO_2$— group;

Cy forms, with the carbon to which it is bonded, a non-aromatic, saturated or unsaturated $C_3-C_{12}$ hydrocarbon ring which is optionally condensed or substituted by one or a number of $(C_1-C_7)$alkyl groups, it being possible for the said groups to substitute the same carbon atom one or a number of times, or by a $C_3-C_6$ spirocycloalkyl;

T represents a $(C_1-C_4)$alkylene which is optionally interrupted by a $(C_3-C_6)$cycloalkylene, the said alkylenes optionally being substituted one or a number of times on the same carbon atom by a $(C_1-C_3)$alkyl; or alternatively T represents a direct bond;

Z represents an —$NR_{11}R_{12}$ group; —$^+NR_{11}R_{12}(C_1-C_4)$-alkyl $(A^-)$, $(A^-)$ being an anion, preferably $Cl^-$, $Br^-$, $I^-$ or $CH_3SO_4^-$; —$N(O)R_{11}R_{12}$; a —$COOR_{11}$ group; an —$NR_{11}COR_{12}$ group; a benzyloxycarbonylamino; a —$CONR_{11}R_{12}$ group; it being understood that when T represents a methylene or a direct bond, Z cannot be —$NR_{11}R_{12}$; —$^+NR_{11}R_{12}(C_1-C_4)$alkyl; —$N(O)R_{11}R_{12}$; —$NR_{11}COR_{12}$; a benzyloxycarbonyl-amino;

$R_{11}$ and $R_{12}$ each independently represent hydrogen; a $(C_1-C_7)$alkyl; a $(C_1-C_4)$alkoxy; a $(C_3-C_7)$cycloalkyl; a phenyl; a $(C_1-C_3)$alkylenecycloalkyl, in which the cycloalkyl is $C_3-C_7$, or a $(C_1-C_3)$alkylenephenyl, it being possible for the said groups optionally to be mono- or polysubstituted by $R_{13}$;

or alternatively $R_{11}$ and $R_{12}$ optionally form, with the nitrogen atom to which they are bonded, a heterocycle chosen from azetidine, pyrrolidine, piperidine, piperazine, piperazinone, morpholine, morpholinone, thiomorpholine and hexahydroazepine heterocycles, which heterocycle is optionally mono- or polysubstituted by $R_{13}$; or a thiomorpholine 1,1-dioxide or a thiomorpholine 1-oxide; or alternatively $R_{12}$ represents a pyrrolidone or a piperidone;

$R_{13}$ represents a hydroxyl group; a $(C_1-C_4)$alkyl; a $(C_1-C_4)$-alkoxy; a mercapto; a $(C_1-C_4)$alkylthio; a $(C_1-C_4)$alkylsulphinyl; a $(C_1-C_4)$alkylsulphonyl; a benzyloxy; a hydroxyalkyloxy; an $NR_{14}R_{15}$ group in which $R_{14}$ and $R_{15}$ each independently represent hydrogen or a $(C_1-C_4)$alkyl or a $(C_1-C_4)$alkyloxycarbonyl or a benzyloxycarbonyl; a carboxyl; a $(C_1-C_4)$ alkyloxycarbonyl; a phenoxycarbonyl; a benzyloxycarbonyl; a carbamoyl; an amidino; a guanidino; an imidazolyl; a thienyl; a pyridyl; an indolyl; or a tetrahydroisoquinolyl;

and to their salts, solvates or hydrates.

It has to be noted that the compounds of formula (I) in which $R_3$ and $R_4$ are hydrogen are known compounds and that the compounds in which -O-T-Z is

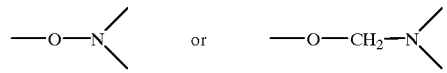

are not stable and thus do not belong to the invention.

Among these compounds, are preferred those of following formula (Ia):

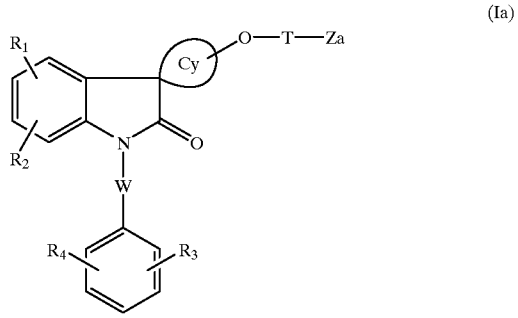

(Ia)

in which:

$R_1$ to $R_4$, W, T and Cy are as defined above for the compounds of formula (I);

Za represents an —$NR_{11}R_{12}$ group; —$^+NR_{11}R_{12}(C_1-C_4)$-alkyl $(A^-)$, $(A^-)$ being an anion, preferably $Cl^-$, $Br^-$, $I^-$ or $CH_3SO_4^-$; —$N(O)R_{11}R_{12}$; a —$COOR_{11}$ group; an —$NR_{11}COR_{12}$ group; a benzyloxycarbonylamino; a —$CONR_{11}R_{12}$ group;

$R_{11}$ and $R_{12}$ each independently represent hydrogen; a $(C_1-C_7)$alkyl; a $(C_1-C_4)$alkoxy; a $(C_3-C_7)$cycloalkyl; a phenyl; a $(C_1-C_3)$alkylenecycloalkyl, in which the cycloalkyl is $C_3-C_7$, or a $(C_1-C_3)$alkylenephenyl, it being possible for the said groups optionally to be mono- or polysubstituted by $R_{13}$;

or alternatively $R_{11}$ and $R_{12}$ optionally form, with the nitrogen atom to which they are bonded, a heterocycle chosen from azetidine, pyrrolidine, piperidine, piperazine, piperazinone, morpholine, morpholinone, thiomorpholine and hexahydroazepine heterocycles, which heterocycle is optionally mono- or polysubstituted by $R_{13}$; or a thiomorpholine 1,1-dioxide or a thiomorpholine 1-oxide;

$R_{13}$ represents a hydroxyl group; a $(C_1-C_4)$alkoxy; a thiol; a $(C_1-C_4)$alkylthio; a $(C_1-C_4)$alkylsulphinyl; a $(C_1-C_4)$alkylsulphonyl; an —$NR_{14}R_{15}$ group in which $R_{14}$ and $R_{15}$ each independently represent hydrogen or a $(C_1-C_4)$alkyl; a carboxyl; a carbamoyl; an amidino; a guanidino; an imidazolyl; a thienyl; a pyridyl; an indolyl; or a tetrahydroisoquinolyl; and to their salts.

The solvates and hydrates of the compounds of above formula (Ia) are also preferred.

In the compounds of formula (Ia), when R represents a methylene or a direct bond, Z cannot be —$NR_{11}R_{12}$; —$^+NR_{11}R_{12}(C_1-C_4)$alkyl; —$N(O)R_{11}R_{12}$; —$NR_{11}COR_{12}$; a benzyloxycarbonylamino.

According to the present invention, "$(C_1-C_7)$alkyl" or "$(C_1-C_6)$alkyl" is understood to mean a straight or branched alkyl having 1 to 7 carbon atoms or 1 to 6 carbon atoms respectively.

The non-aromatic $C_3-C_{12}$ hydrocarbon rings comprise optionally terpenic, saturated or unsaturated, condensed or bridged, mono- or polycyclic radicals. These radicals are optionally mono- or polysubstituted by a $(C_1-C_4)$alkyl. The monocyclic radicals include cycloalkyls, for example cyclopropyl, cyclobutyl, cyclopentyl, cyclohexyl, cycloheptyl, cyclooctyl and cyclododecyl. The polycyclic radicals include, for example, norbornane, adamantane, hexahydroindane, norbornene, dihydrophenalene, bicyclo[2.2.1]heptane, bicyclo[3.3.1]nonane or tricyclo[5.2.1.02,6]decane.

The constituent phenyl group of the $R_1$, $R_2$, $R_3$, $R_4$, $R_5$, $R_6$, $R_7$, $R_8$, $R_9$, $R_{10}$, $R_{11}$ and $R_{12}$ substituents can be unsubstituted, mono- or disubstituted by a $(C_1-C_7)$alkyl, preferably methyl, a trifluoromethyl, a $(C_1-C_7)$alkoxy, preferably methoxy or ethoxy, or a halogen or trisubstituted by a $(C_1-C_7)$alkyl, a $(C_1-C_7)$alkoxy or a halogen.

According to the present invention, halogen is understood to mean an atom chosen from fluorine, chlorine, bromine or iodine, preferably fluorine or chlorine.

When a compound according to the invention has one or more asymmetric carbons, the optical isomers of this compound form an integral part of the invention.

When a compound according to the invention exhibits stereoisomerism, for example of axial-equatorial type or Z-E, the invention comprises all the stereoisomers of this compound.

The salts of the compounds of formula (I) according to the present invention comprise those with inorganic or organic acids which make possible suitable separation or crystallization of the compounds of formula (I), such as picric acid, oxalic acid or an optically active acid, for example a tartaric acid, a dibenzoyltartaric acid, a mandelic acid or a camphorsulphonic acid, and those which or a $(C_1-C_3)$ alkylenephenyl, it being possible for the said groups optionally to be mono- or polysubstituted by $R_{13}$;

or alternatively $R_{11}$ and $R_{12}$ optionally form, with the nitrogen atom to which they are bonded, a heterocycle chosen from azetidine, pyrrolidine, piperidine, piperazine, piperazinone, morpholine, morpholinone, thiomorpholine and hexahydroazepine heterocycles, which heterocycle is optionally mono- or polysubstituted by $R_{13}$; or a thiomorpholine 1,1-dioxide or a thiomorpholine 1-oxide;

$R_{13}$ represents a hydroxyl group; a $(C_1-C_4)$alkoxy; a thiol; a $(C_1-C_4)$alkylthio; a $(C_1-C_4)$alkylsulphinyl; a $(C_1-C_4)$alkylsulphonyl; an —$NR_{14}R_{15}$ group in which $R_{14}$ and $R_{15}$ each independently represent hydrogen or a $(C_1-C_4)$alkyl; a carboxyl; a carbamoyl; an amidino; a guanidino; an imidazolyl; a thienyl; a pyridyl; an indolyl; or a tetrahydroisoquinolyl; and to their salts.

The solvates and hydrates of the compounds of above formula (Ia) are also preferred.

In the compounds of formula (Ia), when R represents a methylene or a direct bond, Z cannot be —$NR_{11}R_{12}$; —$^+NR_{11}R_{12}(C_1-C_4)$alkyl; —$N(O)R_{11}R_{12}$; —$NR_{11}COR_{12}$; a $(C_1-C_4)$alkyloxycarbonylamino; a benzyloxycarbonylamino.

According to the present invention, "$(C_1-C_7)$alkyl" or "$(C_1-C_6)$alkyl" is understood to mean a straight or branched alkyl having 1 to 7 carbon atoms or 1 to 6 carbon atoms respectively.

The non-aromatic $C_3-C_{12}$ hydrocarbon rings comprise optionally terpenic, saturated or unsaturated, condensed or bridged, mono- or polycyclic radicals. These radicals are optionally mono- or polysubstituted by a $(C_1-C_4)$alkyl. The monocyclic radicals include cycloalkyls, for example cyclopropyl, cyclobutyl, cyclopentyl, cyclohexyl, cycloheptyl, cyclooctyl and cyclododecyl. The polycyclic radicals include, for example, norbornane, adamantane, hexahydroindane, norbornene, dihydrophenalene, bicyclo[2.2.1]heptane, bicyclo[3.3.1]nonane or tricyclo[5.2.1.02,6]decane.

The constituent phenyl group of the $R_1$, $R_2$, $R_3$, $R_4$, $R_5$, $R_6$, $R_7$, $R_8$, $R_9$, $R_{10}$, $R_{11}$ and $R_{12}$ substituents can be unsubstituted, mono- or disubstituted by a $(C_1-C_7)$alkyl, preferably methyl, a trifluoromethyl, a $(C_1-C_7)$alkoxy, preferably methoxy or ethoxy, or a halogen or trisubstituted by a $(C_1-C_7)$alkyl, a $(C_1-C_7)$alkoxy or a halogen.

According to the present invention, halogen is understood to mean an atom chosen from fluorine, chlorine, bromine or iodine, preferably fluorine or chlorine.

When a compound according to the invention has one or more asymmetric carbons, the optical isomers of this compound form an integral part of the invention.

When a compound according to the invention exhibits stereoisomerism, for example of axial-equatorial type or Z-E, the invention comprises all the stereoisomers of this compound.

The salts of the compounds of formula (I) according to the present invention comprise those with inorganic or organic acids which make possible suitable separation or crystallization of the compounds of formula (I), such as picric acid, oxalic acid or an optically active acid, for example a tartaric acid, a dibenzoyltartaric acid, a mandelic acid or a camphorsulphonic acid, and those which form physiologically acceptable salts, such as the hydrochloride, the hydrobromide, the sulphate, the hydrogensulphate, the dihydrogenphosphate, the maleate, the fumarate, the 2-naphthalenesulphonate or the para-toluenesulphonate.

The salts of the compounds of formula (I) also comprise salts with organic or inorganic bases, for example the salts of alkali metals or alkaline-earth metals, such as the sodium, potassium or calcium salts, the sodium and potassium salts being preferred, or with an amine, such as trometamol, or alternatively the salts of arginine, of lysine or of any physiologically acceptable amine.

The functional groups optionally present in the molecule of the compounds of formula (I) and the reaction intermediates can be protected, either in a permanent form or in a temporary form, by protective groups which provide for unambiguous synthesis of the expected compounds.

Temporary protective group for amines, alcohols, phenols, thiols or carboxylic acids is understood to mean the protective groups such as those described in Protective Groups in Organic Synthesis, Greene T. W. and Wuts P. G. M., published by John Wiley and Sons, 1991 and in Protective Groups, Kocienski P. J., 1994, Georg Thieme Verlag.

Mention may be made, for example, of the temporary protective groups for amines: benzyls, carbamates, (such as tert-butyloxycarbonyl, which can be cleaved in acid medium, or benzyloxycarbonyl, which can be cleaved by hydrogenolysis), for carboxylic acids (alkyl esters, such as methyl, ethyl or tert-butyl esters, which can be hydrolysed in basic or acid medium, or benzyl esters, which can be hydrogenolysed), for alcohols or for phenols such as tetrahydropyranyl, methoxymethyl or methylethoxymethyl, tert-butyl and benzyl ethers) and reference may be made to the well known general methods described in Protective Groups, cited above.

Preference will be given according to the present invention to the temporary protective groups which can be cleaved in acid medium or in neutral medium by hydrogenolysis.

The permanent protective groups are those which are stable under the cleavage conditions cited above and which are capable of being present in the final products. Such O-protective or N-protective groups are composed of ($C_1$–$C_7$)alkyl or phenyl groups. The permanent N-protective groups also include ($C_1$–$C_5$)alkanoyl groups and aroyl groups, such as benzoyl.

The compounds (I) can contain precursor groups of other functional groups which are generated subsequently in one or a number of other stages.

The compounds of formula (I) wherein the various polar functions, in particular salifiable functions which improve solubility and/or disponibility in water are preferably carried by the -T-Z groups.

The compounds of formula (I) in which the $R_1$ substituent is in the 5-position of the indolin-2-one and in which $R_2$ represents hydrogen are preferred compounds.

The compounds of formula (I) in which $R_1$ is in the 5-position and represents a chlorine atom or an ethoxy group and $R_2$ represents hydrogen are also preferred.

The compounds of formula (I) in which $R_3$ represents hydrogen or a methoxy and $R_4$ represents a methoxy, diethylureido, tert-amylcarbamoyl and tert-butylcarbamoyl group in the 4-position of the benzene ring are preferred compounds. Among these compounds, those in which $R_3$ is in the 2-position are preferred.

The compounds of formula (I) in which Cy represents a cyclohexane and the -O-T-Z group is in the 4-position of the said cyclohexane with respect to the spiro carbon are also preferred.

The compounds of formula:

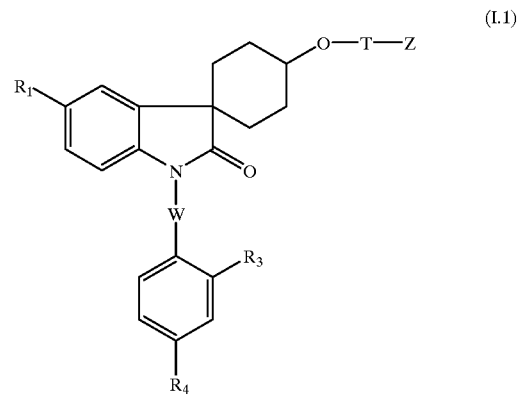

(I.1)

in which $R_1$, $R_3$, $R_4$, W, T and Z are as defined for (I), and their salts, solvates or hydrates are particularly preferred.

The compounds of formula:

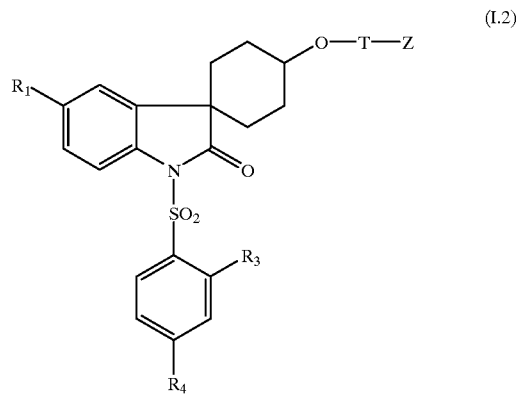

(I.2)

in which $R_1$, $R_3$, $R_4$, T and Z are as defined for (I), and their salts, solvates or hydrates are more particularly preferred.

The compounds of formula:

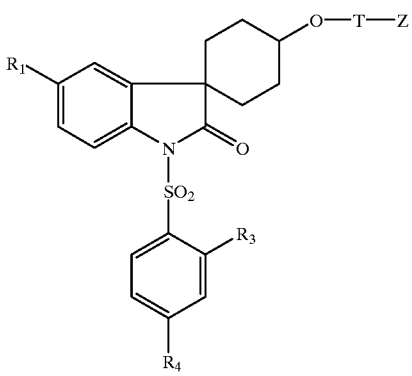

(I.3)

in which R₁, R₃ and R₄ are as defined for (I), T represents a (C₁–C₃)alkylene and Z represents an amino group, a 2-hydroxyethylamino, a 2-(2-hydroxy)ethyloxyethylamino, a morpholinyl or a carboxylic group, and their salts, solvates or hydrates are very particularly preferred.

The compounds of formula:

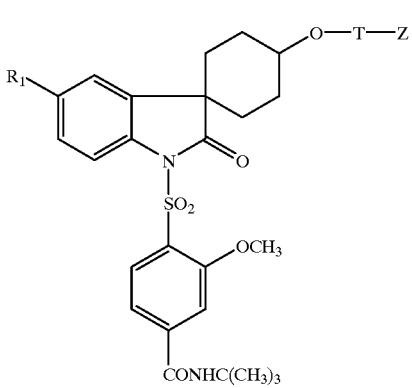

(I.4)

in which R₁, T and Z are as defined for (I), and their salts, solvates or hydrates are more particularly preferred.

The compounds of formulae (I.1), (I.2), (I.3) and (I.4) in which Z has the meaning of Za and the salts thereof are also preferred compounds. It is the same for the solvates and hydrates of these compounds.

The compounds of formulae (I.1), (I.2), (I.3) and (I.4) in which:
  R₁ represents a chlorine atom or an ethoxy group,
  T represents a (C₁–C₃)alkylene and Z represents an amino group, a 2-hydroxyethylamino, a 2-(2-hydroxy) ethyloxyethylamino, a morpholinyl or a carboxylic group, are particularly preferred.

The compounds of formulae (I.1), (I.2), (I.3) in which:
  R₁ represents a chlorine atom or an ethoxy group;
  R₃ represents hydrogen or a methoxy group;
  R₄ represents a methoxy, diethylureido, tert-amylcarbamoyl and tert-butylcarbamoyl, are also preferred.

Among these compounds, those in which T represents a (C₁–C₃)alkylene and Z represents an amino group, a 2-hydroxyethylamino, a 2-(2-hydroxy)ethyloxyethylamino, a morpholinyl or a carboxylic group are preferred.

The products of formula (I), (I.1), (I.2), (I.3) and (I.4) in which Cy represents a cyclohexane and for which the O-T-Z group is in the 4-position of the said cyclohexane with respect to the spiro carbon, in particular the compounds below:

5-chloro-3-spiro-[4-(2-morpholinoethyloxy) cyclohexane]-1-[4-(N-tert-butylcarbamoyl)-2-methoxybenzenesulphonyl]indolin-2-one;

5-ethoxy-3-spiro-[4-(2-aminoethyloxy)cyclohexane]-1-[4-(N-tert-butylcarbamoyl)-2-methoxybenzenesulphonyl]indolin-2-one;

5-ethoxy-3-spiro-[4-(2-(N-methyl-N-(2-hydroxy-ethyl) amino)ethyloxy)cyclohexane]-1-[4-(N-tert-butylcarbamoyl)-2-methoxybenzenesulphonyl]indolin-2-one;

5-ethoxy-3-spiro-[4-(2-morpholinoethyloxy) cyclohexane]-1-[4-(N-tert-butylcarbamoyl)-2-methoxybenzyl]-indolin-2-one;

5-ethoxy-1-[4-(N-tert-butylcarbamoyl)-2-methoxybenzenesulphonyl]-3-spiro-[4-(2-morpholinoethyloxy)-cyclohexane]indolin-2-one;

5-ethoxy-3-spiro-(4-carboxymethyloxycyclohexane)-1-(4-N-tert-butylcarbamoyl-2-methoxybenzenesulphonyl)-indolin-2-one;

5-ethoxy-3-spiro-[4-(2-morpholinoethyloxy) cyclohexane]-1-[4-(N-tert-amylcarbamoyl)-2-methoxybenzenesulphonyl]indolin-2-one;

5-ethoxy-3-spiro-[4-(2-carboxyethyloxy)cyclohexane]-1-[4-(N-tert-amylcarbamoyl)-2-methoxybenzenesulphonyl]indolin-2-one;

5-ethoxy-1-[4-(N',N'N-diethylureido)-2-methoxybenzenesulphonyl]-3-spiro-[4-(2-dimethylaminoethyloxy)-cyclohexane]indolin-2-one;

5-Ethoxy-3-spiro-[4-(2-(4-ethoxypiperidino)-ethyloxy) cyclohexane]-1-[4-(N-tert-butylcarbamoyl)-2-methoxybenzenesulfonyl]indolin-2-one;

5-Ethoxy-3-spiro-[4-(2-glycylaminoethyloxy)-cyclohexane]-1-[4-(N-tert-butylcarbamoyl)-2-methoxybenzenesulfonyl]indolin-2-one;

5-Ethoxy-3-spiro-[4-(2-(N,N-dimethylglycylamino)-ethyloxy)cyclohexane]-1-[4-(N-tert-butylcarbamoyl)-2-methoxybenzenesulfonyl]indolin-2-one;

5-Chloro-3-spiro-[4-(N-(3-dimethylaminopropyl)-carbamoylmethyloxy)cyclohexane]-1-[4-(N-tert-butylcarbamoyl)-2-methoxybenzenesulfonyl]indolin-2-one;

5-Ethoxy-3-spiro-[4-(2-(4-dimethylaminobutyryl-amino) ethyloxy)cyclohexane]-1-[4-(N-tert-butylcarbamoyl)-2-methoxybenzenesulfonyl]indolin-2-one;

5-Ethoxy-3-spiro-[4-(2-(2-hydroxyethylamino)-ethyloxy)cyclohexane]-1-[4-(N-tert-butylcarbamoyl)-2-methoxybenzenesulfonyl]indolin-2-one;

5-Ethoxy-3-spiro-[4-(2-(-L-γ-glutamylamino)-ethyloxy) cyclohexane]-1-[4-(N-tert-butylcarbamoyl)-2-methoxybenzenesulfonyl]indolin-2-one;

5-Ethoxy-3-spiro-[4-(2-(-L-pyroglutamylamino)-ethyloxy)cyclohexane]-1-[4-(N-tert-butylcarbamoyl)-2-methoxybenzenesulfonyl]indolin-2-one;

5-Ethoxy-3-spiro-[4-(2-(2-hydroxyethyloxy)-ethylamino)ethyloxy)cyclohexane]-1-[4-(N-tert-butylcarbamoyl)-2-methoxybenzenesulfonyl]indolin-2-one; and their pharmaceutically acceptable salts, solvates or hydrates are very particularly preferred, being particularly suited to use in pharmaceutical formulations.

The compounds according to the invention can be prepared according to Scheme 1 below.

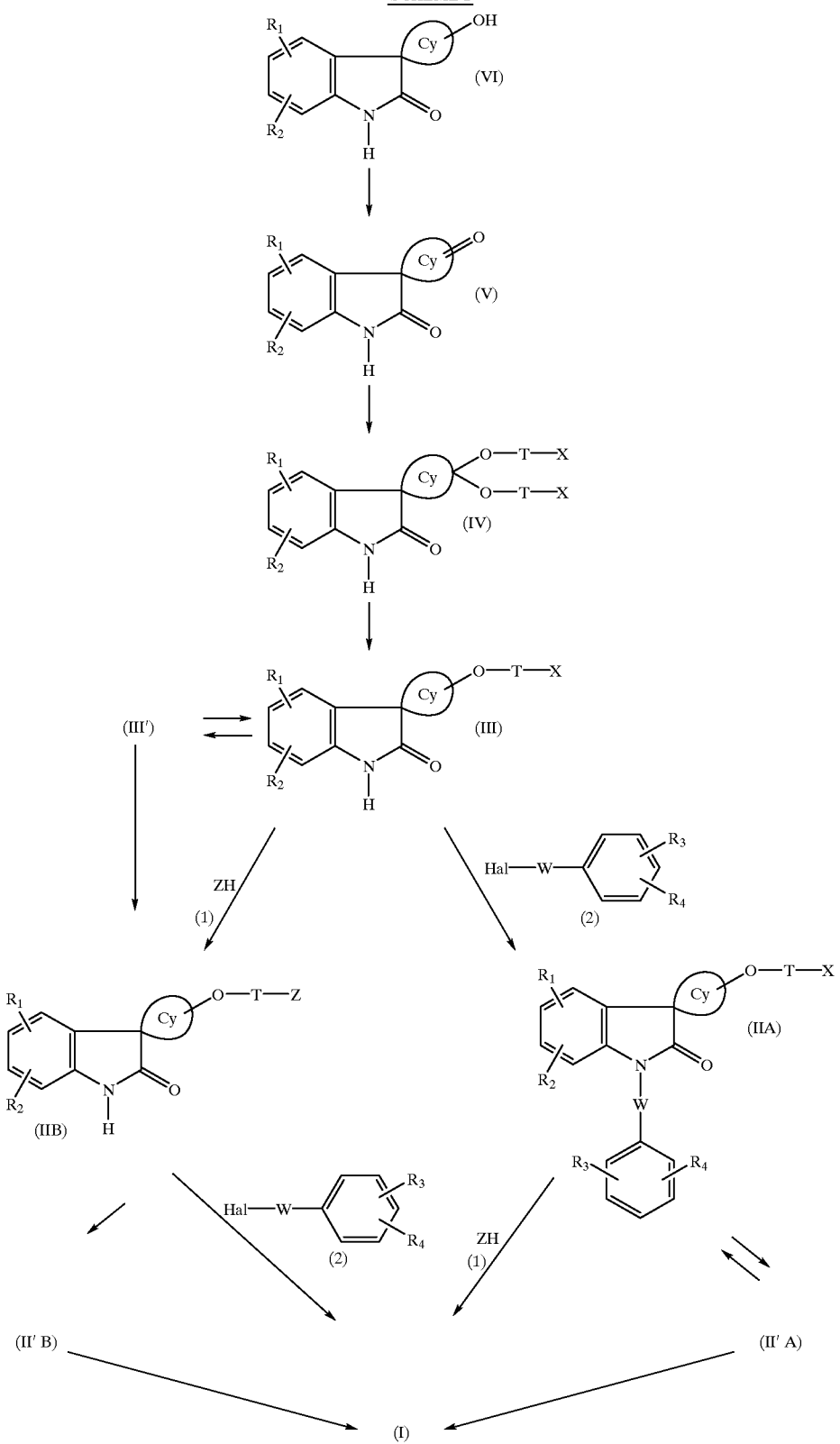

Another subject of the present invention is a process for the preparation of the compounds of formula (I) according to the invention, characterized in that:

(1) either a compound of formula:

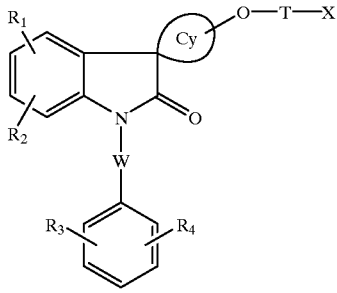

(II A)

in which $R_1$, $R_2$, $R_3$, $R_4$, W, Cy and T are as defined for (I) and in which X is a nucleofuge group, such as a halogen, preferably bromine, chlorine or iodine, or a sulphonic acid derivative, such as tosyloxy or mesyloxy, is reacted with a derivative of formula ZH (1) in which Z is as defined for (I) containing a nucleophilic group capable of displacing X, for example a primary or secondary amine, preferably a secondary amine, in polar solvents, such as dimethylformamide, tetrahydrofuran or acetonitrile, at temperatures of between 0° and 120° C., or alternatively X represents a reducible group, such as an azido, which is subsequently reduced to amino, (2) or, when Z=—COOH, a compound of formula:

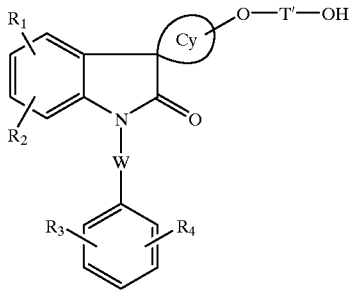

(II'A)

in which $R_1$, $R_2$, W, $R_3$, $R_4$ and Cy are as defined for (I) and T' represents T—CH$_2$—, is reacted with an oxidizing agent, such as chromium oxide in an acid solvent, such as dilute acetic acid at a temperature of between 0° and 100° C., alkali metal dichromates or alkali metal or alkaline-earth metal permanganates;

(3) or a compound of formula:

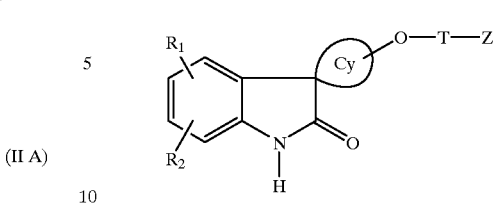

(II B)

in which $R_1$, $R_2$, Cy, T and Z are as defined for (I), is reacted with a compound of formula:

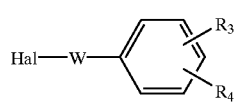

(2)

in which W, $R_3$ and $R_4$ are as defined for (I) and Hal represents a halogen atom, in the presence of a metal hydride, such as, for example, sodium hydride, or an alkali metal alkoxide, such as, for example, potassium tert-butoxide, at temperatures of between −40° and 25° C., in an anhydrous solvent such as tetrahydrofuran;

(4) or, when Z=—COOH, a compound of formula:

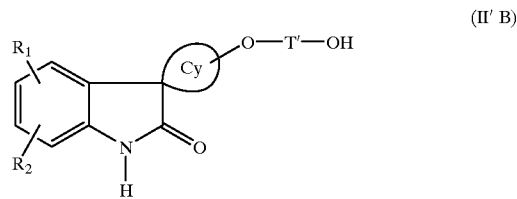

(II' B)

in which $R_1$, $R_2$ and Cy are as defined above for (I) and T' represents T—CH$_2$, is reacted with an oxidizing agent described above for the conversion of (II'A) to (I), then the acid thus obtained of formula:

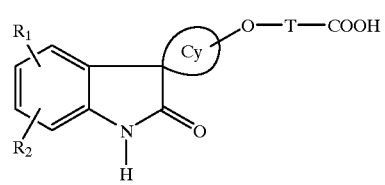

(II" B)

in which $R_1$, $R_2$, Cy and T are as defined above for (I), is subsequently optionally protected by a protective group for the carboxylic acid, in order to obtain the intermediate of formula:

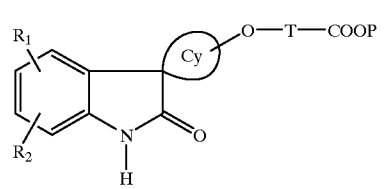

(II" BP)

in which $R_1$, $R_2$, Cy and T are as defined for (I) and P represents a protective group chosen from an alkyl, such as a tert-butyl or a benzyl, and, finally, this compound (II"BP) is subjected to the action of a derivative of formula (2) in order to obtain, after deprotection, a compound (I); which is optionally converted to one of its salts according to techniques well known to the person skilled in the art.

The compounds (II A) and (II B) can be prepared from the compounds (III) according to the following Scheme 2:

halogen, the halide (II A) can be converted to alcohol (II' A) by substitution by a nitrate ion, which is subsequently reduced in the presence of a metal catalyst, such as palladium-on-charcoal, according to the method described in J. Med. Chem., 1995, 38, 130–136.

The compounds of formula (II' A) can also be prepared from the corresponding indolin-2-ones (III') by reaction with

SCHEME 2

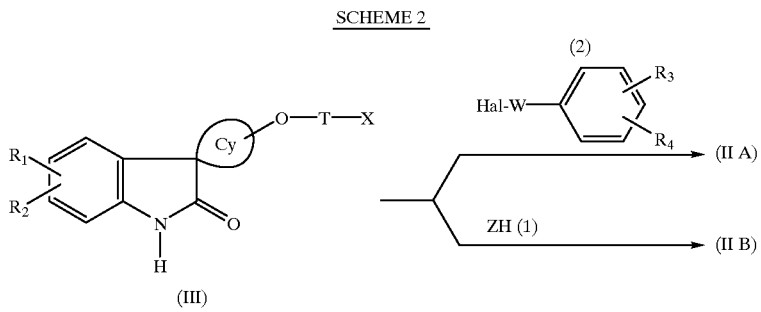

The compounds (II A) can be prepared from the indolin-2-one (III) with a benzenesulphonyl halide, when W represents an —SO$_2$— group, or with a benzyl halide, when W represents a —CH$_2$— group, in an anhydrous solvent, such as dimethylformamide or tetrahydrofuran, in the presence of a metal hydride, such as sodium hydride, or of an alkali metal alkoxide, such as, for example, potassium tert-butoxide, at temperatures of between −40° and 25° C.

The compounds (II A) can also be prepared from the alcohols (II' A) according to known general methods. Mention may be made, for example, of the triphenylphosphine/carbon tetrachloride system according to Angew. Chem. Int. Ed., 1975, 14, 801 or the triphenylphosphine/C(Hal)$_4$ system, in which Hal represents a halogen, in the presence of pyridine according to Carbohyd. Res., 1978, 61, 511 or by reaction with an aryl- or alkylsulphonyl halide in the presence of a base in an inert solvent. The X groups can be exchanged: for example, a sulphonate group can be converted to a halide, such as an iodine derivative, by reaction with an alkali metal iodide, such as sodium iodide, according to J. Chem. Soc., 1949, 326. When X represents a the reactants (2) under the conditions already described for the conversion of the compounds (III) to (II A). The alcohol group of (III') will be temporarily protected (compounds III' P), for example by a protective group, such as methyl or tetrahydropyranyl, according to EP 636,608.

The compounds (II B) can be prepared from the indolin-2-one (III) by substitution of the nucleofuge group X by a ZH derivative (1), such as, for example, a primary or secondary amine, in polar solvents, such as dimethylformamide, tetrahydrofuran or acetonitrile, at temperatures of between 0° and 120° C., according to the nature of the nucleophile and of the nucleofuge.

The compounds (II B) for which —T—Z represents —T—COOH are prepared from an alcohol (III') in which T' represents T—CH$_2$— by oxidizing the alcohol (III') according to the conditions described for the conversion of (II' A) to (I).

The compounds (III) are novel and form part of the invention. They can be prepared according to the reaction Scheme 3 below:

SCHEME 3

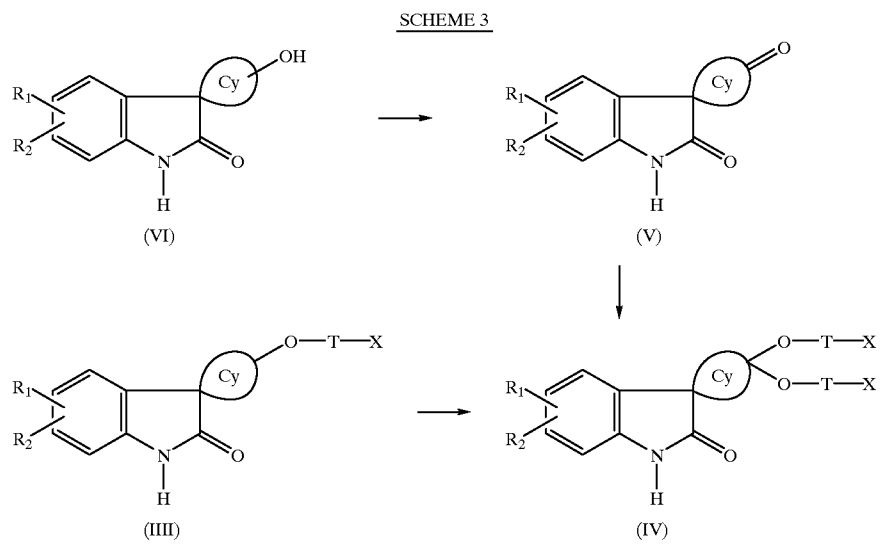

Thus, the indolin-2-ones (III) can be obtained by reduction of the acetals (IV) under mild conditions, for example according to the method described in J. Org. Chem., 1987, 52, 2594–2596, by the action of zinc borohydride in the presence of trimethylsilyl chloride in ethers or chlorinated solvents, such as, for example, dichloromethane, or by the action of the dimethyl sulphide.BH₃ complex in the presence of trimethylsilyl triflate in ethers or dichloromethane according to the method described in J. Org. Chem., 1993, 58, 6756–6765, or from the alcohols (III'):

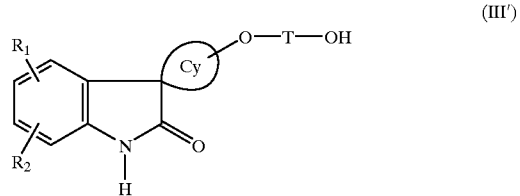

(III')

in which $R_1$, $R_2$, Cy and T are as defined for (I), according to the methods cited above for the conversion of (II' A) to (II A).

The acetals (IV) are prepared by well known reactions, for example from a ketone (V) with an alcohol by acid catalysis in dehydrating medium. The preparation can be carried out by azeotropic removal of water or in the presence of molecular sieves, according to Synthesis, 1972, 419.

The ketones (V) can be prepared from the corresponding secondary alcohols (VI) according to numerous methods well known to the person skilled in the art involving, for example, oxidizing agents, such as chromium oxide in acetic acid medium or chromium oxide complexes, such as pyridinium chlorochromate, in inert solvents, such as ethyl acetate or dichloromethane, or alternatively by hydrolysis of the acetals (IV').

The alcohols (VI) can be obtained from the corresponding compounds in which the hydroxyl group is protected, for example by a methoxymethyl or tetrahydropyranyl group. These compounds are described in EP 636,608 or are obtained similarly. The compounds thus protected of formula:

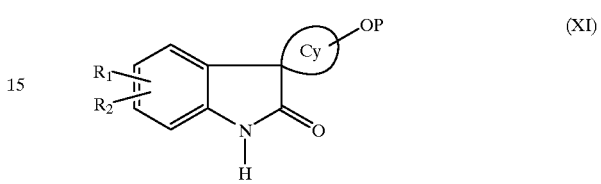

(XI)

are subjected to an acid hydrolysis in an alcohol, such as methanol or ethanol, or in an ether, such as tetrahydrofuran, at temperatures of between −5° and 70° C.

The compounds (III') can be prepared according to Scheme 4 below:

SCHEME 4

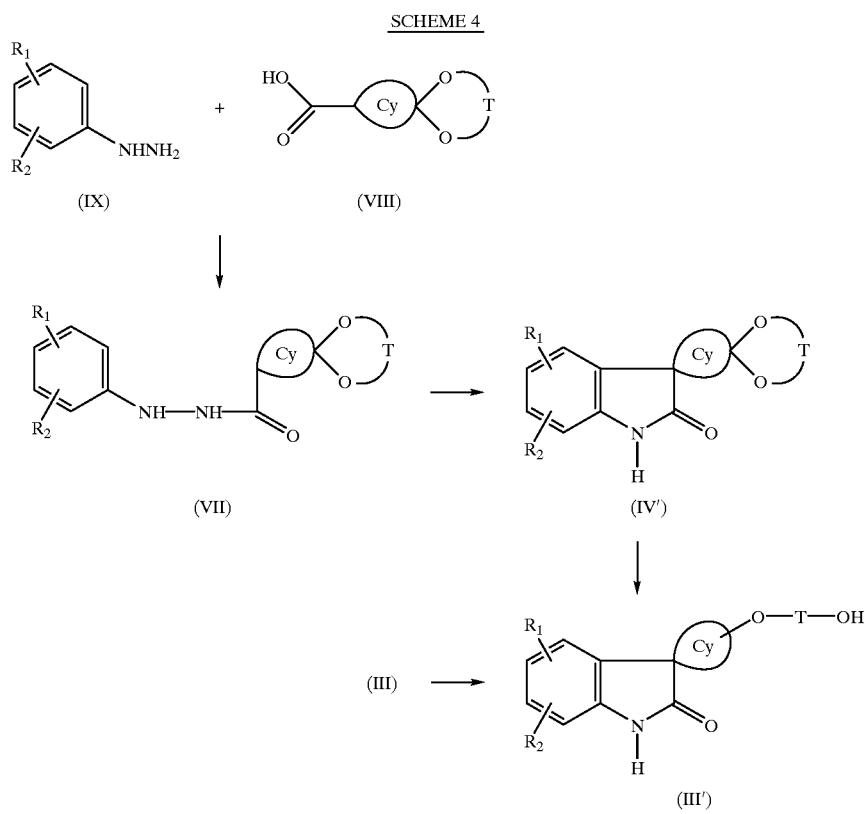

As for the preparation of the compounds (III) from the acetals (IV), the compounds (III') can be prepared from a cyclic acetal (IV'), such as a dioxolane, which is obtained from a hydrazide (VII).

A halide (III) can also be converted to (III') according to the methods already cited for the conversion of the compounds (II A) to compounds (II' A).

Unlike, and as for the conversion of the compounds (II'A) to compounds (II A) according to the methods already cited, the alcohols (III') can also be converted to compounds (III) wherein X is a nucleofuge group such as alkyl or benzenesulphonate by reaction with an alkyl halide or a phenylsulphonyl halide in inert solvents in the presence of a tertiary amine or in pyridine.

The compounds (III') can be converted to compounds (III'P) in which the alcohol group is protected as indicated above. The compounds (III'P) can also be converted to compounds (II A) wherein X is a temporary protected alcohol according to reactions previously described.

The compounds (IV') in which T is at least equal to —$CH_2CH_2$— can be prepared from the ketones (V) by reaction with a diol HO-T-OH according to the conditions mentioned for the conversion of (V) to (IV). The compounds (IV') can also be obtained directly from the corresponding hydrazides (VII) by a Brunner reaction described by Moore R. F. et al., J. Chem. Soc., 1951, 3475–3478, for example by heating in solvents, such as quinoline, in the presence of a metal or alkaline-earth metal oxide, such as calcium oxide. The reaction can also be carried out by heating in inert solvents, such as tetralin, naphthalene or 1,2,3,4-tetramethylbenzene, according to the method described by Wolff J. et al., Tetrahedron, 1986, 42, (15), 4267–4272, starting with a lithium salt prepared beforehand in an inert solvent, such as tetrahydrofuran, at low temperature.

These phenylhydrazide derivatives (VII) can be obtained from a phenylhydrazine (IX), which are known compounds or compounds prepared according to known methods, and from derivatives of the carboxylic acids (VIII), such as the esters, chlorides or mixed anhydrides obtained by reaction of an alkyl chloroformate, preferably isobutyl chloroformate, in the presence of a base according to conventional methods well known to the person skilled in the art. The acids (VIII) are known or prepared according to known methods.

An alternative for the synthesis of the compounds (I) in which T represents —$CH_2$— and Z represents a —$COOZ_1$ group in which $Z_1$ represents hydrogen, a ($C_1$–$C_3$)alkyl or a benzyl comprises the use of an alcohol of formula:

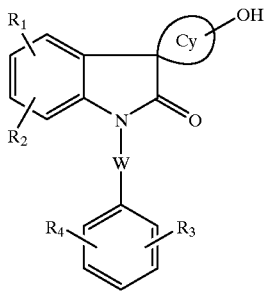

(II C)

in which $R_1$, $R_2$, $R_3$, $R_4$, W and Cy are as defined for (I), which are known products or products prepared according to EP 636,609, which are alkylated with a powerful alkylating agent, such as a trifluoromethanesulphonate of formula $CF_3SO_2$—$CH_2$—COOAlk (3) generated in situ by reaction of silver triflate with the corresponding halogenated derivative in which Alk represents a ($C_1$–$C_4$)alkyl, in halogenated solvents, such as dichloromethane or carbon tetrachloride, in the presence of a base, such as 2,6-di-tert-butylpyridine, according to the method described for alkyl trifluoromethanesulphonates in Carbohydrate Research, 1975, 44, $C_5$–$C_7$.

The ester thus obtained can be exchanged or cleaved under the general conditions already mentioned.

The alcohols (II C) can be prepared according to the following Scheme 5:

SCHEME 5

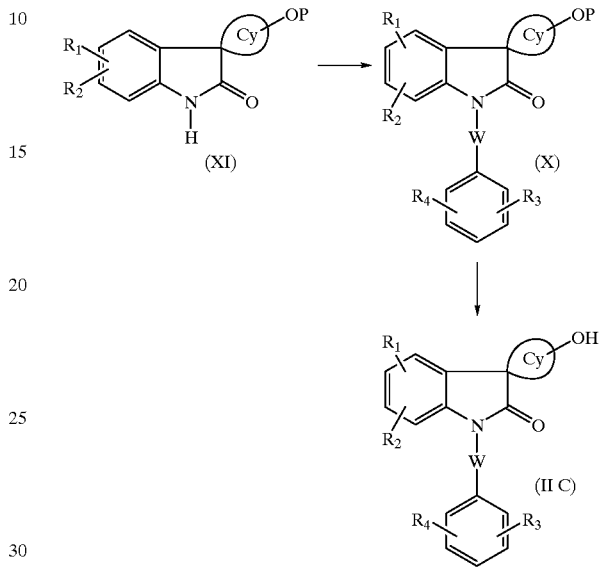

The alcohols (II C) can be prepared from the protected compounds (X) by deprotection under the same conditions as for the conversion of the compounds (XI) to compounds (VI).

The compounds (X) are obtained from the compounds (XI) according to the method described in EP 636,608 with the halides (2) according to the conditions already described for the conversion of the compounds (II B) to (I) and the compounds (III) to (II A).

A compound of formula (I) can also be converted to another compound of formula (I) carrying a polyfunctional residue as defined for Z, in particular for —$NR_{11}COR_{12}$ or for —$CONR_{11}R_{12}$, the reaction being carried out according to known methods for peptide synthesis described, for example, by Bodansky M. in Principles of Peptide Synthesis 2nd ed., 1993 and Bodansky M. in Peptide Chemistry, Springer Verlag; thus, these methods make it possible to avoid the racemization of asymmetric centres possibly carried by the amino acids.

The reactants ZH of formula (1) are commercially available or prepared according to known methods.

The derivatives of formula (2):

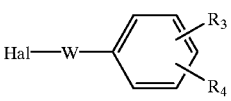

are also prepared according to known methods. In particular, the benzenesulphonyl halides in which W=—$SO_2$— and $R_3$ and $R_4$ are as defined above for (I) are prepared by known methods. Thus, for example, 4-dimethylaminobenzenesulphonyl chloride is prepared according to Sukenik C. N. et al., J. Am. Chem. Soc., 1977, 99, 851–858. More generally, benzenesulphonyl halides substituted by a dimethylamino group are known or prepared by known methods; 4-benzyloxybenzenesulphonyl chloride is prepared according to EP 229,566.

The alkoxybenzenesulphonyl chloride is prepared from the sodium alkoxybenzenesulphonate, itself prepared by reacting an alkyl halide with sodium hydroxybenzenesulphonate.

The benzenesulphonyl halides are obtained according to Col. Czechoslov. Chem. Commun., 1984, 49, 1184, from the aniline derivatives substituted by the same group, the said aniline derivatives themselves being obtained from the corresponding nitro derivatives.

The benzenesulphonyl halide (2) in which the substituent in the 4-position represents an —NHCON($CH_2CH_3$)$_2$ group can be prepared by reacting chlorosulphonic acid with N',N'-diethyl-N-phenylurea, itself obtained by reacting aniline with diethyl-carbamoyl chloride.

In the case where $R_3$ or $R_4$ represent an N-substituted carbamoyl, it is possible to condense a compound (2) in which $R_3$ is a carboxylic acid precursor, such as N-benzylcarbamoyl, to deprotect the protective group by hydrogenolysis and then to condense with the desired amine or alternatively directly to prepare (2) in which $R_3$ has the expected value. The reaction is generally carried out from the correctly chosen anilines, themselves being obtained by reduction of the corresponding nitro derivatives.

The anilines are diazotized under conventional conditions by nitrous acid and reacted with $SO_2$ in the presence of cupric chloride according to J. Heterocyclic Chem., 1986, 23, 1253.

The benzyl halides in which W represents —$CH_2$— are known or prepared according to known methods. Mention may be made, for example, of J. V. Rajanbabu, J. Org. Chem., 1986, 51, 1704–1712 and the publications cited in EP 636,609.

The halomethylbenzene derivatives can generally be prepared by reacting N-halosuccinimides with the corresponding methylbenzene derivatives and according to EP 229,566.

The reaction is carried out in a solvent, such as carbon tetrachloride, in the presence of dibenzoyl peroxide. It is also possible to prepare a halomethylbenzene derivative from a corresponding hydroxymethylbenzene derivative by reacting with phosphorus tribromide in ether or by reacting with thionyl chloride.

The compounds (3) are obtained from an alkyl iodoacetate and from a trifluoromethanesulphonic acid salt, such as the silver salt, according to Chem. Reviews, 1977, 77.

The quaternary ammoniums, the N-oxide and S-oxide derivatives and the sulphones of the compounds (I) are part of the invention and are prepared conventionally by reaction respectively with an alkyl halide or by oxidation with hydrogen peroxide or a peracid, such as peracetic acid or metachloroperbenzoic acid, in inert solvents.

The compounds of formula (I) can comprise amine or acid functions which can be converted to amide functions by reacting respectively with acid derivatives or amine derivatives which can comprise asymetric carbons. Mention can be made to the unracemizing coupling reactions well known to the person skilled in the art, in particular in the peptide synthesis, and reference may be made to Wunsch E. in Methoden der Organischen Chemie (Synthese von Peptiden), 1974, 15, band 1+2, Thieme Verlag, Stuttgart or to Jones J. H., in The Peptides, 1979, 1, 65–104, Gross E., Meienhofer J., Academic Press, ou M. Bodansky, Principles of Peptide Synthesis and Peptide Chemistry, 1993, Springer Verlag.

The compounds of formula (I) above also comprise those in which one or a number of hydrogen, carbon or halogen, in particular chlorine or fluorine, atoms have been replaced by their radioactive isotope, for example tritium or carbon-14. Such labelled compounds are useful in research, metabolic or pharmacokinetic studies or in biochemical tests as receptor ligands.

The affinity of the compounds according to the invention for the V1 receptors of vasopressin was determined in vitro by using the method described in Lynch C. J. et al., J. Biol. Chem., 1985, 260 (5), 2844–2851. This method consists in studying the displacement of tritiated vasopressin bonded to the V1 sites of rat liver membranes.

Likewise, the affinity of the compounds (I) according to the invention for oxytocin receptors was determined in vitro by displacement of a radioiodinated oxytocin analog bonded to the receptors of a membrane preparation from the mammary glands of gestating rats, according to a technique similar to that described by Elands J. et al., in Eur. J. Pharmacol., 1987, 147, 197–207.

The affinity of the compounds (I) according to the invention for the $V_2$ receptors was measured on a bovine kidney membrane preparation according to a method adapted from Crause P. et al., Molecular and Cellular Endocrinology, 1982, 28, 529–541 and from Stassen F. L. et al., J. Pharmacol. Exp. Ther., 1982, 233, 50–54.

The compounds according to the invention inhibit the binding of tritiated arginine-vasopressin to the receptors of the membrane preparation. The $IC_{50}$ values of the compounds according to the invention are low, generally ranging from $10^{-5}$ to $10^{-9}$M.

The agonist or antagonist activity for vasopressin receptors of the compounds according to the invention, administered orally, was evaluated in the normally hydrated rat (Sprague-Dawley strain) according to the technique described in Br. J. Pharmacol., 1992, 105, 787–791. The diuretic effect, generally observed for the compounds of formula (I) and, for some of these compounds, at doses of less than or equal to 10 mg/kg, shows that the compounds of formula (I) constitute a series of powerful $V_2$ antagonists.

The compounds according to the invention are active after administration by different routes, in particular by the oral route.

No sign of toxicity was observed with these compounds at the pharmacologically active doses and their toxicity is thus compatible with their medical use as medicines.

The compounds according to the present invention make it possible either to mimic or to inhibit, selectively, the effects of vasopressin and/or of oxytocin. Among these compounds, antagonists of vasopressin receptors can intervene in the regulation of the central and peripheral circulation, in particular coronary, renal and gastric circulations, and in water regulation and the release of the adrenocorticotropic hormone (ACTH). The vasopressin agonists can advantageously replace vasopressin or its analogues in the treatment of diabetes insipidus; they can also be used in the treatment of enuresis and in the regulation of haemostasis: treatment of haemophilia or of von Willebrand's syndrome or platelet aggregant antidote, Laszlo F. A., Pharmacol. Rev., 1991, 43, 73–108, Drug Investigation, 1990, 2 (suppl. 5), 1–47. The hormones themselves: vasopressin and oxytocin and some of their peptide or nonpeptide analogues are used in therapeutics and have demonstrated their effectiveness (Vasopressin. Gross P. et al., published by John Libbey Eurotext, 1993, in particular 243–257 and 549–562. Laszlo F. A. and Laszlo F. A. Jr., Clinical Perspectives for Vasopressin Antagonists, Drug News Perspect., 1993, 6 (8); North W. G., J. Clin. Endocrinol., 1991, 73, 1316–1320. Legros J. J. et al., Prog. NeuroPharmacol. Biol. Psychiat., 1988, 12, 571–586; Andersson K. E. et al., Drugs Today, 1988, 24 (7), 509–528; Stump D. L. et al., Drugs, 1990, 39, 38–53; Caltabiano S. et al., Drugs Future, 1988, 13, 25–30; Mura Y. et al., Clin. Nephrol. 1993, 40, 60–61; Faseb J., 1994, 8 (5), A587: 3398).

This type of $V_2$ antagonist molecules with an aquaretic profile has a wide range of therapeutic indications and constitutes a major innovation in the treatments of cardiac insufficiency, hyponatraemias, water disorders, water retentions, and the like. This type of compound can advantageously replace conventional diuretics in all pathologies where they are recommended in man and in animals. It is also possible, with such molecules, to envisage the treatment of hypertension in combination with antihypertensives from other therapeutic classes, such as, for example, B-blockers, inhibitors of the converting enzyme or alternatively antagonists of angiotensin II receptors.

Thus, the compounds according to the invention are useful particularly in the treatment of complaints of the central and peripheral nervous systems, of the cardiovascular system, of the endocrinal and hepatic system, of the renal area, of the gastric, intestinal, and pulmonary area, in ophthalmology and in disorders of sexual behaviour, in man and in animals.

Another subject of the present invention is therefore pharmaceutical compositions containing an effective dose of a compound according to the invention, or of a pharmaceutically acceptable salt, solvate or hydrate of the latter, and suitable excipients.

The said excipients are chosen according to the pharmaceutical formulation and the method of administration desired.

In the pharmaceutical compositions of the present invention for oral, sublingual, subcutaneous, intramuscular, intravenous, topical, intratracheal, intranasal, transdermal, rectal or intraocular administration, the active principles of formula (I) above, or their possible salts, solvates or hydrates can be administered as unit administration formulations, as a mixture with conventional pharmaceutical vehicles, to animals and to man for the prophylaxis or the treatment of the above disorders or diseases. Appropriate administration unit dosages comprise formulations by the oral route, such as tablets, gelatin capsules, powders, granules and oral solutions or suspensions, sublingual, buccal, intratracheal or intranasal administration formulations, subcutaneous, intramuscular or intravenous administration formulations and rectal administration formulations. For topical application, the compounds according to the invention can be used in creams, ointments, lotions or eye washes.

In order to obtain the desired prophylactic or therapeutic effect, the dose of active principle can vary between 0.01 and 50 mg per kg of body weight per day.

Each unit dose can contain from 0.5 to 1000 mg, preferably from 1 to 500 mg, of active ingredients in combination with a pharmaceutical vehicle. This unit dose can be administered 1 to 5 times per day so as to administer a daily dosage of 0.5 to 5000 mg and preferably of 1 to 2500 mg.

When a solid composition is prepared in the form of tablets, the main active ingredient is mixed with a pharmaceutical vehicle, such as gelatin, starch, lactose, magnesium stearate, talc, gum arabic or the like. The tablets can be coated with sucrose, with a cellulose derivative or with other appropriate materials or alternatively they can be treated so that they have a sustained or delayed activity and so that they continuously release a predetermined amount of active principle.

A preparation in gelatin capsules is obtained by mixing the active ingredient with a diluent and by pouring the mixture obtained into soft or hard gelatin capsules.

A preparation in the form of a syrup or an elixir or for administration in the form of drops can contain the active ingredient in conjunction with a sweetener, preferably a calorie-free sweetener, methylparaben and propylparaben as antiseptic as well as an agent which gives taste and an appropriate dye.

Water-dispersible powders or granules can contain the active ingredient as a mixture with dispersing agents or wetting agents, or suspending agents, such as polyvinylpyrrolidone, as well as with sweeteners or taste correctors.

For rectal administration, recourse is had to suppositories which are prepared with binders which melt at rectal temperature, for example cocoa butter or poly(ethylene glycol)s.

For parenteral administration, use is made of aqueous suspensions, isotonic saline solutions or sterile injectable solutions which contain pharmacologically compatible dispersing and/or wetting agents, for example propylene glycol or butylene glycol.

The active principle can also be formulated in the form of microcapsules, optionally with one or a number of vehicles or additives, or alternatively with matrices, such as a polymer or a cyclodextrin (patch or sustained-release compositions).

The compositions according to the invention can be used in the treatment or the prevention of different vasopressin-dependent or oxytocin-dependent complaints and in dysfunctions of vasopressin or oxytocin secretion, cardiovascular complaints, such as hypertension, pulmonary hypertension, cardiac insufficiency, circulatory insufficiency, myocardial infarction, atherosclerosis or coronary vasospasm, in particular in smokers, unstable anginas and PTCA (percutaneous transluminal coronary angioplasty), cardiac ischaemia, disturbances of haemostasis, in particular haemophilia, or von Willebrand's syndrome; complaints of the central nervous system, migraine, cerebral vasospasm, cerebral haemorrhage, cerebral oedemas, depression, anxiety, bulimia, psychotic states or memory disorders, for example; renopathies and renal dysfunctions, such as oedemas, renal vasospasm, renal cortex necrosis, nephrotic syndrome, hyponatraemia, hypokalaemia, diabetes, Schwartz-Bartter syndrome or renal lithiasis; complaints of the gastric system, such as gastric vasospasm, hepatocirrhosis, ulcers, the pathology of vomiting, for example nausea, including the nausea due to chemotherapy, travel sickness, or alternatively the syndrome of inappropriate secretion of antidiuretic hormone (SIADH), diabetes insipidus and enuresis; complaints of the hepatic system, such as cirrhoses of the liver; abdominal ascites and all the disorders inducing abnormal water retention, suprarenal disorders (Cushing's disease) and in particular hypercorticism and hyperaldosteronaemia. The compositions according to the invention can also be used in the treatment of disorders of sexual behaviour, in the weight excess and obesity by favourably replacing the usual diuretics already used for this indication. In woman, the compositions according to the invention can be used for treating dysmenorrhoea or premature labour. The compositions according to the invention can also be used in the treatment of small-cell lung cancers, hyponatraemic encephalopathies, Raynaud's disease, Meniére's syndrome, pulmonary syndrome, glaucoma and the prevention of cataracts and in postoperative treatments, in particular after abdominal, cardiac or hemorrhagic surgery.

The compositions of the present invention can contain, in addition to the products of formula (I) above or their pharmaceutically acceptable salts, solvates or hydrates, other active principles which can be used in the treatment of the disorders or diseases indicated above.

Thus, another subject of the present invention is pharmaceutical compositions containing a number of active principles in combination, one of which is a compound according to the invention.

Thus, according to the present invention, pharmaceutical compositions can be prepared which contain a compound according to the invention in combination with a compound which acts on the renin-angiotensin system, such as an inhibitor of the converting enzyme, an angiotensin II antagonist or a renin inhibitor. A compound according to the invention can also be combined, for example, with a peripheral vasodilator, a calcium inhibitor, a β-blocker, an $\alpha_1$-blocker or diuretic. Such compositions will be useful in particular in the treatment of hypertension or heart failure. Two compounds according to the invention can also be combined: a specific antagonist of the $V_1$ receptor with a specific antagonist of oxytocin or a $V_1$ antagonist and a $V_2$ antagonist or a $V_2$ antagonist and $V_1$ agonist.

The compositions of the present invention advantageously contain a product of formula (I.1), (I.2), (I.3) or (I.4) above or one of its pharmaceutically acceptable salts, solvates or hydrates. Each of these compounds can also be combined with a specific angiotensin II antagonist, preferably with irbesartan.

These combinations will make it possible to reinforce the therapeutic activities of the compounds according to the invention.

The following PREPARATIONS and EXAMPLES illustrate the invention without, however, limiting it.

The nuclear magnetic resonance spectra were performed in DMSO-d6 except as otherwise mentioned at 200 MHz and the chemical shifts were expressed in ppm.

The following abbreviations are used:

s=singulet m=multiplet t=triplet q=quintuplet

PREPARATION I

Alcohols of formula (VI)

5-Ethoxy-3-spiro-(4-hydroxycyclohexane)indolin-2-one. Compound (VI.1)

A solution of 22 g of 5-ethoxy-3-spiro-(4-methoxymethyloxycyclohexane)indolin-2-one, prepared according to EP 636,608 in 130 ml of methanol and 9 ml of concentrated hydrochloric acid (36%) is heated at 40° C. for 3 hours. The reaction mixture is cooled and the precipitate is then successively filtered off, rinsed with diethyl ether and dried to obtain the polar isomer of the expected product; M.p.=225° C. 50 ml of water are added to the filtrate and then, successively, the methanol is evaporated, extraction is carried out with dichloromethane and the organic phases are washed with water, dried and evaporated to obtain the expected pro-duct in the form of a mixture of isomers; M.p.=170° C.

5-Chloro-3-spiro-(4-hydroxycyclohexane)indolin-2-one. Compound (VI.2)

The preparation is carried out according to the same procedure as above, from 5-chloro-3-spiro-(4-methoxymethyloxycyclohexane)indolin-2-one prepared from 5-chloro-indolin-2-one according to the method described in EP 636,608. The expected product is isolated, after extraction with dichloromethane, in the form of a mixture of isomers; M.p.=260° C.

PREPARATION II

Ketones of formula (V)

5-Ethoxy-3-spiro-(4-oxocyclohexane)indolin-2-one. Compound (V.1)

3.8 g of 5-ethoxy-3-spiro-(4-hydroxycyclohexane)-indolin-2-one (VI.I) (mixture of isomers) and 5.8 ml of pyridine are dissolved in 250 ml of ethyl acetate and 6.3 g of pyridinium chlorochromate, adsorbed on 29 g of neutral alumina, are added. The reaction mixture is then stirred at 25° C. for 16 hours, filtration is then carried out and the solvent is evaporated from the filtrate. 3.4 g of the expected product are isolated after recrystallization from toluene in the presence of active charcoal; M.p.=168° C.

5-Chloro-3-spiro-(4-oxocyclohexane)indolin-2-one. Compound (V.2)

This compound is prepared according to the same procedure as for the preparation of Compound (V.1) from 5-chloro-3-spiro-(4-hydroxycyclohexane)indolin-2-one (VI.2); M.p.=220° C.

PREPARATION III

Acetals of formula (IV)

5-Ethoxy-3-spiro-[4,4-di(2-chloroethyloxy)-cyclohexane]indolin-2-one. Compound (IV.1)

3 g of 5-ethoxy-3-spiro-(4-oxocyclohexane)indolin-2-one (V.1) are dissolved in 30 ml of toluene and 4.6 ml of 2-chloroethanol, 20 g of 5 Å molecular sieve and 0.22 g of methanesulphonic acid are added. The reaction mixture is slowly stirred for 18 hours at 20° C., filtration is then carried out and the molecular sieve is rinsed with dichloromethane. The solvent is evaporated and the expected product is then crystallized from diethyl ether; M.p.=170° C.

5-Ethoxy-3-spiro-[4,4-di(3-chloropropyloxy) cyclohexane]indolin-2-one. Compound (IV.2)

The preparation is carried out according to the same procedure as for the preparation of Compound (IV.1) from the same ketone (V.1) and 3-chloropropanol; M.p.=147° C.

5-Chloro-3-spiro-[4,4-di(2-chloroethyloxy)-cyclohexane]-indolin-2-one. Compound (IV.3)

The preparation is carried out according to the same procedure as for the preparation of Compound (IV.1) from Compound (V.2) and 2-chloroethanol; M.p.=174° C.

PREPARATION IV

Derivatives of formula (III)

5-Ethoxy-3-spiro-[4-(3-chloropropyloxy)cyclohexane]-indolin-2-one (mixture of isomers). Compound (III.1)

2.2 ml of a 0.29M solution of zinc borohydride in diethyl ether (prepared according to the method described in Chem. Pharm. Bull., 1984, 32 (4), 1411–1415) are slowly added at 0° C. to 0.55 g of acetal (IV.2) in 3 ml of dichloromethane, followed by 0.34 ml of trimethyl-chlorosilane. The reaction mixture is stirred for 16 hours at 20° C. and then, successively, 10 ml of a saturated $NaHCO_3$ solution is added, extraction is carried out with ethyl acetate and the organic phases are washed with a saturated NaCl solution. After drying over $MgSO_4$ and evaporation, 0.4 g of an oil is isolated, which oil is chromatographed on silica gel, elution being carried out with an 8/2 (v/v) cyclohexane/ethyl acetate mixture. The expected product is isolated (mixture of isomers) in the form of a resin.

$^1$H NMR, CDCl$_3$, 200 MHz: 7.75 (s, 1H), 7.03 (d, 0.25H), 6.83 (d, 0.75H), 6.79–6.65 (m, 3H), 4.06–3.9 (q, 2H), 3.72–3.58 (m, 4H), 3.54–3.50 (m, 1H), 2.18–1.53 (m, 1OH), 1.37 (t, 3H).

5-Ethoxy-3-spiro-[4-(2-chloroethyloxy)cyclohexane]-indolin-2-one (mixture of isomers). Compound (III.2)

The preparation is carried out according to the same procedure as for the preparation of Compound (III.1) from Compound (IV.1).

$^1$H NMR, CDCl$_3$, 200 MHz: 8 (s, 1H), 6.85–6.63 (m, 3H), 4.03–3.93 (q, 2H), 3.81–3.74 (m, 2H), 3.70–3.58 (m, 3H), 2.21–1.55 (m, 8H), 1.4 (t, 3H).

5-Chloro-3-spiro-[4-(2-chloroethyloxy)cyclohexane]-indolin-2-one (mixture of isomers). Compound (III.3)

The preparation is carried out according to the same procedure as for the preparation of Compound III.1 from Compound (IV. 3).

$^1$H NMR, DMSO-d6 200 MHz: 10.49 (s, 0.25H), 10.39 (s, 0.75H), 7.40 (s, 1H), 7.21–7.16 (d, 1H), 6.81–6.77 (d, 1H), 3.7 (m, 4H), 3.55 (m, 1H), 1.96–1.61 (m, 8H).

5-Ethoxy-3-spiro-[4-(2-tosyloxy)cyclohexane]-indolin-2-one. Compound (III.4)

17.97 g of tosyl chloride are added at 0° C. to 19,25 g of compound (III'1) described in preparation X in 130 ml of pyridine. The reaction mixture is stirred at 20° C. for 3 hours. The reaction mixture is poured into 650 ml of water and then stirred for 30 minutes. 28.06 g of the expected product are isolated after filtration, washings with water and drying at 40° C. under vacuum in the presence of phosphoric anhydre. The product obtained from the polar isomer (III'1) melts at 152° C.

PREPARATION V

Derivatives of formula (II A)

5-Ethoxy-1-[4-(N-tert-butylcarbamoyl)-2-methoxybenzenesulphonyl]-3-spiro-[4-(2-chloroethyloxy)-cyclohexane]indolin-2-one (mixture of isomers). Compound (IIA.1)

0.29 g of potassium tert-butoxide is added to a solution, cooled to −60° C., of 0.75 g of chlorinated derivative (III.2) and 0.75 g of 4-(N-tert-butylcarbamoyl)-2-methoxybenzenesulphonyl chloride in 90 ml of tetrahydrofuran. The temperature is allowed to rise to 20° C., the reaction mixture is stirred for 2 hours, 30 ml of a 15% NaCl solution are then added and, successively, extraction is carried out with ethyl acetate, the organic phases are washed with a 15% NaCl solution, the organic phases are dried over MgSO$_4$, the solvent is evaporated and the residue is chromatographed on silica gel, elution being carried out with an 85/15 (v/v) cyclohexane/ethyl acetate mixture, to isolate the expected product in the form of a resin.

$^1$H NMR, DMSO-d6 200 MHz: 8 (m, 2H), 7.5 (m, 3H), 7.04 (s, 0.75H), 6.85 (m, 1.25H), 4.0 (q, 2H), 3.6 (s, 3H), 3.66 (s, 4H), 3.58 (s, 3H), 3.5 (m, 1H), 1.9–1.6 (m, 8H), 1.34 (s, 9H), 1.28 (t, 3H).

5-Ethoxy-1-[4-(N',N'-diethylureido)-2-methoxybenzenesulphonyl]-3-spiro-[4-(2-tosyloxyethyloxy)-cyclohexane]indolin-2-one. Compound (II A.2)

0.25 g of tosyl chloride is added at 0° C. to a solution of 0.18 ml of triethylamine and 0.25 g of 5-ethoxy-1-[4-(N',N'-diethylureido)-2-methoxybenzenesulphonyl]-3-spiro-[4-(2-hydroxyethyloxy)cyclohexane]-indolin-2-one (prepared in EP 0,636,608) in 3 ml of anhydrous tetrahydrofuran. The reaction mixture is stirred for 48 hours at 20° C., 10 ml of a saturated NaHCO$_3$ solution are added and then, successively, extraction is carried out with ethyl acetate, the organic phases are dried over MgSO$_4$, the solvent is evaporated and the residue is chromatographed on silica gel, eluent: 99/1 (v/v) and then 95/5 dichloromethane/methanol; M.p.=80° C.

5-ethoxy-1-[4-(N-tert-butylcarbamoyl)-2-methoxybenzenesulphonyl]-3-spiro-[4-(2-tosyloxyethyloxy)-cyclohexane]indolin-2-one. Compound (II A.3)

The expected product is isolated in a similar way as for the preparation of the compound (II A.2) starting from 5-ethoxy-1-[4-(2-hydroxyethyloxy)cyclohexane]indolin-2-one or by reacting 4-(N-tert-butylcarbamoyl)-2-methoxybenzenesulphonyl chloride with the compound (III.4) in the conditions described for the preparation of the compound (II A.1); M.p.=142° C.

PREPARATION VI

Alcohols of formula (II'A)

5-Ethoxy-3-spiro-[4-(2-hydroxyethyloxy) cyclohexane]-1-[4-(N-tert-butycarbamoyl)-2-methoxybenzenesulphonyl]-indolin-2-one. Compound (II' A.1)

a) 5-Ethoxy-3-spiro-[4-(2-nitrooxyethyloxy) cyclohexane]-1-[4-(N-tert-butylcarbamoyl)-2-methoxybenzenesulphonyl]indolin-2-one. Compound (II'A.1)

A mixture of 0.6 g of Compound (II A.1), 0.8 g of silver nitrate and 0.25 g of sodium iodide in 10 ml of acetonitrile is heated at reflux for 48 hours. The salts are separated by filtration and the solvents are evaporated. The expected product is isolated by chromatography on silica gel, elution being carried out with an 80/20 (v/v) cyclohexane/ethyl acetate mixture; M.p.=80° C. (hydrate).

b) 0.5 g of the above nitrate, 0.5 ml of cyclohexene and 0.5 g of 10% palladium-on-charcoal are heated at reflux for 1 hour in 15 ml of ethanol, the catalyst is then separated by filtration, the solvent is evaporated and the residue is chromatographed on silica gel, elution being carried out with dichloromethane and then with a 99/1 (v/v) dichloromethane/methanol mixture. The mixture of isomers of the expected product is isolated; M.p.=120° C. (hemihydrate), followed by the polar isomer, which is crystallized from a mixture of isopropyl ether and ethyl acetate (1/1; v/v); M.p.=189° C. (hydrate).

5-Ethoxy-3-spiro-[4-(3-hydroxypropyloxy)-cyclohexane]-1-[4-(N-tert-amylcarbamoyl)-2-methoxybenzenesulphonyl]indolin-2-one. Compound (II' A.2)

a) 5-Ethoxy-3-spiro-[4-(3-methoxymethyloxy-propyloxy)cyclohexane]-1-[4-(N-tert-amylcarbamoyl)-2-methoxybenzenesulphonyl]indolin-2-one.

5-Ethoxy-3-spiro-[4-(3-methoxymethyloxypropyloxy)-cyclohexane]indolin-2-one (III'.2P) of preparation X is condensed with N-tert-amylcarbamoyl-2-methoxysulphonyl chloride according to the procedure described in PREPARATION V, to obtain the expected product, which is charged as it is to the following stage.

b) A mixture of 0.5 g of Compound prepared in a) in 1.5 ml of methanol and 0.2 ml of concentrated hydrochloric acid (36%) is heated at 50° C. for 1 hour. 5 ml of water are added, extraction is carried out with ethyl acetate, the solvents are then evaporated and the expected product is then isolated after chromatography on silica gel, elution being carried out with a 1/1 (v/v) cyclohexane/ethyl acetate mixture; M.p.=120° C.

PREPARATION VII

Indolin-2-one of formula (II.B)

5-Chloro-3-spiro-[4-(2-morpholinoethyloxy)-cyclohexane]indolin-2-one (mixture of isomers). Compound (II B.1)

A mixture of 0.57 g of Compound (III.3), 0.5 g of morpholine and 0.27 g of NaI in 6 ml of dimethylformamide is heated for 24 hours at 85° C. 10 ml of water are added to the reaction mixture and 10 ml of a saturated NaHCO3 solution are added and then, successively, extraction is carried out twice with ethyl acetate, the organic phases are dried over $MgSO_4$, the solvent is evaporated and the residue is chromatographed on silica gel, elution being carried out with dichloromethane and then with a 98/2 (v/v) dichloromethane/methanol mixture, to isolate 0.5 g of the expected product in the form of an oil.

$^1$H NMR: 10.4 (s, 1H), 7.4 (s, 1H), 7.2 (d, 1H), 6.8 (d, 1H), 3.6 (m, 7H), 2.4 (m, 6H), 1.9–1.6 (m, 8H).

5-Ethoxy-3-spiro-[4-(2-N-tert-butyloxycarbonyl-N-(benzyloxycarbonylmethyl)amino)ethyloxy)cyclohexane]-indolin-2-one (mixture of isomers). Compound (II B.2)

1.5 g of tosylate (III.4) (mixture of isomers), 0.66 g of benzyl glycinate hydrochloride and 0.35 of sodium carbonate in 80 ml of acetonitrile are heated at 60° C. for 48 hours. The solvent is evaporated under reduced pressure, the residue is taken up with 40 ml of ethyl acetate, the organic phase is washed with water, dried over $Na_2SO_4$ and the solvent is evaporated. The residue is chromatographied on silica gel, elution being carried out with a 99/1 (v/v) dichloromethane/methanol mixture and a resin is isolated which is dissolved in 20 ml of dioxane. 0.13 g of MgO and 0.539 g of di-tertbutyldicarbonate dissolved in 10 ml of dioxane are added at 5° C. and the reaction mixture is stirred at 20° C. for 16 hours. The solvent is evaporated, the residue is taken up with ethyl acetate, the organic phase is washed successively with a buffer solution of pH=2, a saturated sodium bicarbonate solution and water.

The drying is carried out on $Na_2SO_4$ and the solvent is evaporated. After purification by chromatography on silica gel, elution being carried out with a 5/5 (v/v) ethyl acetate/cyclohexane mixture, the expected product is obtained in the form of a resin.

$^1$H RMN: 10.12 (s, 0.3H); 10.03 (s, 0.7H); 7.30 (m, 5H); 6.88 (d, 1H); 6.70 (d, 2H); 5.14 (s, 0.7H); 5.12 (s, 0.3H); 4.05 (m, 2H); 3.95 (q, 2H); 3.3 to 3.6 (m, 5H); 1.4 to 2.1 (m, 8H); 1.2 to 1.4 (m, 12H).

5-Ethoxy-3-spiro-[4-(2-N-tert-butyloxycarbonyl-amino)ethyloxy)cyclohexane]indolin-2-one. Compound (II B.3)

a) 5-ethoxy-3-spiro-[4-(2-aminoethyloxy)cyclohexane]-indolin-2-one.

A mixture of 1.5 g of the compound (III.4) (obtained from the polar isomer (III'1), and 0.23 g of sodium azide in 15 ml of dimethylformamide is heated at 50° C. for 16 hours. 30 ml of water are added, extraction is carried out twice with ethyl acetate. The organic phases are dried over $Na_2SO_4$, the solvent is evaporated partially under reduced pressure until a volume of about 20 ml. Said solution is hydrogenated at 60° C. under a pressure of $10^6$ Pa in the presence of 0.6 g of Lindlar catalyst (Palladium over $CaCO_3$). The catalyst is filtered off and the solvent is evaporated under reduced pressure. The residue is chromatographied on a silica gel column, elution being carried out with a 90/10 (v/v) dichloromethane/methanol mixture. The hydrate hydrochloride of the expected product is isolated after recristallization of the base in ethyl acetate followed by hydrochloration in ethyl acetate; M.p.=168° C.

b) 0.4 ml of 2N sodium hydroxide, 0.05 g of magnesium oxide and 0.19 g of di-tert-butyldicarbonate dissolved in 7 ml of dioxane are added successively at about +5° C. to 0.27 g of the previous compound in 20 ml of dioxane. After having stirred for 2 hours at 20° C., the solvent is evaporated, and then the residue is taken up with ethyl acetate, the organic phase is washed successively with a buffer solution of pH=2, a saturated sodium bicarbonate solution and water. The drying is carried out on $Na_2SO_4$, the solvent is evaporated and the expected product is isolated in the form of a resin.

$^1$H RMN: 10.02 (s, 1H); 6.91 (s, 1H); 6.68 (s, 2H); 3.92 (q, 2H); 3.55–3.35 (m, 3H); 3.05 (m, 2H); 2.05–1.45 (m, 8H); 1.36 (s, 9H); 1.27 (t, 3H).

PREPARATION VIII

Hydrazides of formula (VII)

N'-(4-Ethoxyphenyl)-4,4-ethylenedioxycyclohexane)-carbohydrazide. Compound (VII.1)

1.65 ml of isobutyl chloroformate are added, at −40° C., to a mixture of 2.63 g of sodium 4,4-ethylenedioxycyclohexaneoate in 20 ml of tetrahydrofuran, followed by 1.8 ml of triethylamine. The reaction mixture is stirred for 2 hours at 0° C., 2.4 g of 4-ethoxyphenylhydrazine hydrochloride are then added at −20° C., the reaction mixture is stirred for 2 hours at 0° C., 100 ml of water are then added and extraction is carried out with ethyl acetate. The organic phases are washed successively with water, with a $KHSO_4$ solution (pH 2) and with a saturated potassium carbonate solution, dried over $MgSO_4$ and evaporated. The expected product is obtained after crystallization from diethyl ether; M.p.=158° C.

N'-phenyl-4,4-ethylenedioxycyclohexanecarbohydrazide. Compound (VII.2)

Likewise, the compound (VII.2) is isolated from the phenylhydrazine. M.p.=158° C.

PREPARATION IX

Acetals of formula (IV')

5-Ethoxy-3-spiro-(4,4-ethylenedioxycyclohexane)-indolin-2-one. Compound IV'.1

2.15 ml of a 1.6M solution of butyllithium in hexane are added at −50° C. to a suspension of 1 g of the hydrazide (VII.1) in 16 ml of tetrahydrofuran. The reaction mixture is stirred for 15 minutes and 16 ml of tetralin are added. The tetrahydrofuran is distilled off and heating is carried out at 180° C. for 45 minutes. 20 ml of ethyl acetate are then added at room temperature and then, successively, washing is carried out with water, the organic phase is dried over $MgSO_4$, the solvents are distilled off under vacuum and the residue is chromatographed on silica gel, elution being carried out with a 7/3 (v/v) cyclohexane/ethyl acetate mixture. The expected product is isolated by crystallization from diethyl ether; M.p.=183° C.

The same product is also obtained by reaction of 5-ethoxy-3-spiro-(4-oxocyclohexane)indolin-2-one (Compound V.1) with ethylene glycol in cyclohexane in the presence of 5 Å molecular sieve and a catalytic amount of para-toluenesulphonic acid.

5-Ethoxy-3-spiro-(4,4-propylenedioxycyclohexane)-indolin-2-one. Compound (IV'.2)

The preparation is carried out according to the same procedure described above for the preparation of Compound (IV'.1) from the corresponding hydrazide or by reaction of 5-ethoxy-3-spiro-(4-oxocyclohexane)indolin-2-one (Compound (V.1)) with 1.3-propanediol in cyclohexane in the presence of 5 Å molecular sieve and of a catalytic amount of para-toluenesulphonic acid; M.p.=216° C.

3-Spiro-(4,4-ethylenedioxycyclohexane)indolin-2-one. Compound IV'3

The preparation is carried out according to the same procedure as above for the preparation of the compound (IV'1) starting from the corresponding hydrazide (VII.2); M.p.=218° C.

PREPARATION X
Alcohols of formula (III') and (III' P)

5-Ethoxy-3-spiro-[4-(2-hydroxyethyloxy)cyclohexane]-indolin-2-one. Compound (III'.1)

20.2 ml of a 0.25M solution of zinc borohydride in diethyl ether (prepared according to the method described in Chem. Pharm. Bull., 1984, 32 (4), 1411–1415) are added slowly at 0° C. to 3.1 g of acetal IV'.1 in 20 ml of dichloromethane, followed by 2.8 ml of trimethylsilyl chloride. The reaction mixture is stirred for 16 hours at 20° C., 20 ml of a saturated NaHCO$_3$ solution are then added and, successively, the solvents are evaporated, extraction is carried out with ethyl acetate, drying is carried out over MgSO$_4$, the solvent is evaporated and the residue is purified by chromatography on silica gel, elution being carried out with a 67/34 (v/v) cyclohexane/ethyl acetate mixture. The mixture of isomers of the expected product is isolated, followed by the polar isomer which is crystallized from diethyl ether; M.p.=125° C.

5-Ethoxy-3-spiro-[4-(3-hydroxypropyloxy)-cyclohexane]indolin-2-one. Compound (III'.2)

The preparation is carried out according to the same procedure as above for the preparation of Compound (III'.1) from the acetal (IV'.2). The polar isomer of the expected product is obtained; M.p.=180° C. (hemihydrate).

5-Ethoxy-3-spiro-[4-(3-methoxymethyloxypropyloxy)-cyclohexane]indolin-2-one. Compound (III'.2P)

A solution of 1 g of 5-ethoxy-3-spiro-[4-(3-hydroxypropyloxy)cyclohexane]indolin-2-one (III'.2), 7.7 ml of dimethoxymethane, 0.065 g of LiBr and 0.07 g of para-toluenesulphonic acid in 15 ml of dichloromethane is stirred for 24 hours at room temperature and 10 ml of a saturated NaCl solution are added. Separation is carried out and the organic phase is dried over MgSO$_4$ and the solvent is distilled off to obtain the polar isomer of the expected product after chromatography on silica gel, elution being carried out with a 1/1 (v/v) cyclohexane/ethyl acetate mixture; M.p.=89° C.

PREPARATION XI
Protected alcohols of formula (X)

5-Ethoxy-3-spiro-(4-methoxymethyloxycyclohexane)-1-[4-(N-tert-butylcarbamoyl)-2-methoxybenzenesulphonyl]-indolin-2-one. Compound (X.1)

0.283 g of potassium tert-butoxide is added to a solution, cooled to −40° C., of 5-ethoxy-3-spiro-(4-methoxymethyloxycyclohexane)indolin-2-one (Compound of formula (XI)), prepared according to EP 636,608, in 80 ml of tetrahydrofuran. The temperature is allowed to rise to 0° C., the mixture is then cooled to −40° C. and 0.73 g of (2-methoxy-4-N-tert-butylcarbamoyl)benzenesulphonyl chloride in 7 ml of tetrahydrofuran is added. The reaction mixture is stirred for 2 hours at room temperature and then, successively, 20 ml of water are added, extraction is carried out with ethyl acetate, drying is carried out over MgSO$_4$, the solvent is evaporated and the oil obtained is purified by chromatography on silica gel, elution being carried out with an 8/2 (v/v) cyclohexane/ethyl acetate mixture. The at least polar isomer of the expected product is isolated; M.p.=165° C., followed by the polar isomer; M.p.=156° C.

PREPARATION XII
Alcohols of formula (IIc)

5-Ethoxy-3-spiro-(4-hydroxycyclohexane)-1-[4-(N-tert-butylcarbamoyl)-2-methoxybenzenesulphonyl]indolin-2-one. Compound (IIc.1)

A mixture of the polar isomer of Compound (X.1) in 1.2 ml of methanol and 0.24 ml of concentrated hydrochloric acid (36%) is heated at 50° C. for 1 hour. 8 ml of water are added to the reaction mixture and then, successively, extraction is carried out with dichloromethane, the organic phases are dried over MgSO$_4$ and the solvents are evaporated. The expected product is obtained after purification by chromatography on silica gel, elution being carried out with dichloromethane; M.p.=268° C. (polar isomer).

In the same way, from the least polar isomer prepared according to (X.1), the least polar isomer of the expected product is isolated; M.p.=130° C. (hemihydrate). Compound (IIc.2)

PREPARATION XIII
Reactants of formula (2)

2-Methoxy-4-N-tert-amylcarbamoylbenzenesulphonyl chloride. Reactant (2).1 a) N-tert-amyl-3-methoxy-4-nitrobenzamide 30 ml of tert-amylamine are added at 10° C. to a solution of 27 g of 3-methoxy-4-nitrobenzoyl chloride (obtained from 25 g of the corresponding acid and thionyl chloride at reflux for 4 hours, followed by evaporation under vacuum) in 250 ml of dichloromethane. The reaction mixture is stirred for 30 minutes at 20° C., 100 ml of a 1N hydrochloric acid solution are then added, the organic phase is separated by settling, washed and dried over MgSO$_4$, the solvent is then evaporated and the residue is chromatographed on silica gel, elution being carried out with dichloromethane, to obtain 31 g of the expected product; M.p.=65° C.

In the same way and from N-tert-butylamine, N-tert-butyl-3-methoxy-4-nitrobenzamide is prepared; M.p.=118° C.

b) N-tert-amyl-3-methoxy-4-aminobenzamide

A mixture of 31 g of N-tert-amyl-3-methoxy-4-nitrobenzamide obtained in a), 20 g of 10% palladium-on-charcoal and 76 ml of cyclohexene in 310 ml of ethanol is heated at reflux for 3 hours. The mixture is filtered and the filtrate is evaporated to obtain 25 g of the expected product; M.p.=108° C.

In the same way, from the compound N-tert-butyl-3-methoxy-4-nitrobenzamide, N-tert-butyl-3-methoxy-4-aminobenzamide is prepared; M.p.=160° C.

c) 2-Methoxy-4-tert-amylcarbamoylbenzenesulphonyl chloride.

A solution of 7.9 g of sodium nitrite in 31 ml of water is added at 0° C. to a solution of 25 g of N-tert-amyl-3-methoxy-4-aminobenzamide in 103 ml of acetic acid and 187 ml of 36% hydrochloric acid. The reaction mixture is stirred for 1 hour at 0° C. and then this solution, stored at 0° C., is added to a suspension of 6.8 g of cupric chloride in 25 ml of water and 140 ml of acetic acid saturated at 0° C. with approximately 69 g of sulphur dioxide. The reaction mixture is stirred at 0° C. for 3 hours and then at 20° C. for 16 hours and the mixture is poured onto 750 g of ice and subsequently stirred for 1 hour at 20° C. The precipitate is filtered off and then successively rinsed with water and dried under vacuum for 48 hours in order to obtain 19 g of the expected product; M.p.=104° C.

4-N-tert-Butylcarbamoyl-2-methoxybenzenesulphonyl chloride. Reactant (2).2

In the same way, from N-tert-butyl-3-methoxy-4-aminobenzamide, the expected reactant is isolated; M.p.=148° C.

3-Methoxy-4-benzyloxycarbonylbenzenesulphonyl chloride. Reactant (2).3

By using the same reaction as above, from the benzyl ester of 4-amino-3-methoxybenzoic acid (M.p.=72° C., resulting from the reduction of the corresponding nitro derivative by tin in hydrochloric acid medium; M.p.=88° C.), the expected reactant is isolated; M.p.=55° C.

N-tert-Butyl-4-bromomethyl-3-methoxybenzamide. Reactant (2).4

A mixture of 3 g of N-tert-butyl-4-methyl-3-methoxybenzamide, 2.4 g of N-bromosuccinimide and 0.16 g of benzoyl peroxide in 40 ml of carbon tetrachloride is stirred at 30° C. while irradiating in the visible spectrum for 48 hours. The solvent is evaporated and then, successively, 25 ml of water are added, extraction is carried out with diethyl ether, drying is carried out over $MgSO_4$, the solvent is evaporated and the residue is chromatographed on silica gel, elution being carried out with an 8/2 (v/v) cyclohexane/ethyl acetate mixture. The expected reactant is isolated after crystallization from isopropyl ether; M.p.=114° C.

EXAMPLE 1

5-Ethoxy-1-[4-(N-tert-butylcarbamoyl)-2-methoxybenzenesulphonyl]-3-spiro-[4-(2-morpholinoethyloxy)cyclohexane]indolin-2-one.

(I): $R_1$=5—$OC_2H_5$; $R_2$=H; $R_3$=2—$OCH_3$; W=$SO_2$;

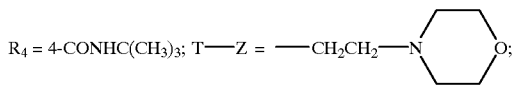

the least polar isomer.

A mixture of 0.6 g of the chlorinated derivative (II A. 1) obtained according to PREPARATION V, 0.26 g of morpholine and 0.15 g of sodium iodide in 6 ml of dimethylformamide is heated at 60° C. under an inert atmosphere for 40 hours. The solvent is evaporated under vacuum and then, successively, the residue is taken up in 20 ml of a 5% aqueous $NaHCO_3$ solution, extraction is carried out with ethyl acetate, the organic phases are washed with a 10% NaCl solution and dried over $MgSO_4$, the solvent is evaporated and a resin is isolated which is chromatographed on silica gel, elution being carried out with a 98/2 (v/v) dichloromethane/methanol mixture.

The least polar isomer of the expected product is isolated (Rf=0.5; silica TLC; 95/5 (v/v) dichloromethane/methanol). The fumarate is prepared in acetone and is crystallized from diethyl ether; M.p.=153° C. (EXAMPLE 1).

$^1$H NMR, DMSO-d6 200 MHz: 8.0 (m, 2H), 7.5 (m, 2H), 7.4 (s, 1H), 6.88 (d, 1H), 6.82 (s, 1H), 6.6 (s, 2H, fumaric acid), 4.0 (q, 2H), 3.6 (s, 3H), 3.55 (m, 7H), 2.45 (m, 6H), 2–1.4 (m, 8H), 1.34 (s, 9H), 1.3 (t, 3H).

EXAMPLE 2

5-Ethoxy-1-[4-(N-tert-butylcarbamoyl)-2-methoxybenzenesulphonyl]-3-spiro-[4-(2-morpholinoethyloxy)cyclohexane]indolin-2-one.

(I): $R_1$=5—$OC_2H_5$; $R_2$=H; $R_3$=2—$OCH_3$; W=$SO_2$;

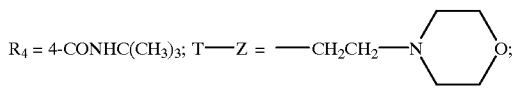

the most polar isomer.

The most polar isomer of the product prepared above according to EXAMPLE 1 is isolated under the above conditions; Rf=0.43; M.p.=212° C.–216° C.

$^1$H NMR, DMSO-d6 200 MHz: 8.0 (m, 2H), 7.5 (m, 2H), 7.4 (s, 1H), 7.03 (s, 1H); 6.84 (d, 1H), 6.6 (s, 2H, fumaric acid), 4.0 (q, 2H), 3.6 (s, 3H), 3.5 (m, 6H), 3.40 (m, 1H), 2.45 (m, 6H), 1.9–1.6 (m, 8H), 1.34 (s, 9H), 1.3 (t, 3H).

The fumarate is prepared in acetone and is crystallized from diethyl ether; M.p.=172° C. (EXAMPLE 2).

Monohydrated dihygenophosphate is prepared by reacting the monohydrated phosphoric acid with the base in ethanol; M.p.=170° C. The nitrate is prepared by reacting aqueous nitric acid with the base in ethanol; M.p.=155° C.

EXAMPLE 3

5-Ethoxy-1-[4-(N',N'-diethylureido)-2-methoxybenzenesulphonyl]-3-spiro-[4-(2-dimethylaminoethyloxy)-cyclohexane]indolin-2-one.

(I): $R_1$=5—$OC_2H_5$; $R_2$=H; $R_3$=2—$OCH_3$; W=$SO_2$;

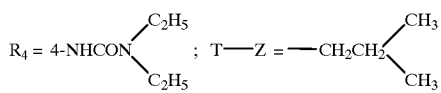

A mixture of 0.23 g of the tosylated derivative (II A.2) obtained above according to PREPARATION V in 3.3 ml of acetonitrile and 0.23 ml of a 40% aqueous dimethylamine solution is stirred for 48 hours at 20° C. 1 ml of a saturated $NaHCO_3$ solution is added and, successively, extraction is carried out with ethyl acetate, drying is carried out over $MgSO_4$, the solvent is evaporated and the residue is chromatographed on silica gel, elution being carried out with a dichloromethane/methanol/aqueous ammonia (245/5/0.2 v/v/v) mixture; (Rf=0.5; silica TLC; 85/15/1 v/v/v dichloromethane/methanol/aqueous ammonia); M.p.=103° C.

EXAMPLE 4

5-Ethoxy-3-spiro-[4-(2-aminoethyloxy)cyclohexane]-1-[4-(4-N-tert-butylcarbamoyl)-2-methoxybenzenesulphonyl] indolin-2-one (mixture of isomers).

(I): $R_1$=5—$OC_2H_5$; $R_2$=H; $R_3$=2—$OCH_3$; W=$SO_2$; $R_4$=4—CONH-C(CH$_3$)$_3$; T-Z=—CH$_2$CH$_2$NH$_2$ a) 5-Ethoxy-3-spiro-[4-(2-azidoethyloxy)cyclohexane]-1-[4-(4-N-tert-butylcarbamoyl)-2-methoxybenzenesulphonyl]-indolin-2-one (mixture of isomers).

A mixture of 0.5 g of the chlorinated derivative (II A.1) obtained above according to PREPARATION V, 0.06 g of sodium azide and 0.126 g of sodium iodide in 5 ml of dimethylformamide is heated at 100° C. under an inert atmosphere for 2 hours. 10 ml of water are added to the reaction mixture, extraction is then carried out with ethyl acetate and, successively, the organic phases are washed with water and dried over Na$_2$SO$_4$ and the solvent is partially concentrated to a volume of 20 ml to obtain an azide solution which is used as it is in the following reaction.

b) The solution obtained in a) is hydrogenated at 40° C. for 60 hours under 10$^6$ Pa in the presence of 0.2 g of palladium/CaCO$_3$ (Lindlar catalyst; 5% Pd). The catalyst is separated by filtration, the solvent is evaporated and the residue is chromatographed on a column of silica gel, elution being carried out with an 8/2 (v/v) dichloromethane/methanol mixture. The expected product is isolated in the base form and is salified with fumaric acid in acetone and crystallized from isopropyl ether to obtain the expected product; M.p.=138° C. (monohydrate).

In the same way, from the compound (II A.3) and by the same steps, the polar isomer of the expected product is isolated, the hemihydrated hydrochloride of which melts at 174° C.

EXAMPLE 5

5-Chloro-3-spiro-[4-(2-morpholinoethyloxy) cyclohexane]-1-[4-(N-tert-butylcarbamoyl)-2-methoxybenzenesulphonyl]indolin-2-one.

(I): R$_1$=5—Cl; R$_2$=H; R$_3$=2—OCH$_3$; W=SO$_2$;

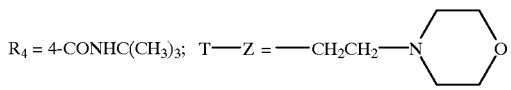

R$_4$ = 4-CONHC(CH$_3$)$_3$;  T—Z = —CH$_2$CH$_2$—N⟨ ⟩O 0.073 g of potassium tert-butoxide is added to a solution, cooled to −30° C., of 0.21 g of Compound (II B.1) obtained above according to PREPARATION VII in 24 ml of tetrahydrofuran. The temperature is allowed to rise to 0° C., the mixture is then cooled to −40° C. and 0.19 g of [2-methoxy-4-(N-tert-butylcarbamoyl)]benzenesulphonyl chloride in 2 ml of tetrahydrofuran is added. The reaction mixture is then stirred for 2 hours at −10° C., 15 ml of water are added and then, successively, extraction is carried out with ethyl acetate, drying is carried out over MgSO$_4$, the solvent is evaporated and the residue is purified by chromatography on silica gel, elution being carried out with dichloromethane and then with a 96/4 dichloromethane/methanol mixture. The polar isomer of the expected product is isolated and is salified with fumaric acid in acetone. The fumarate is crystallized from diisopropyl ether; M.p.=107° C. (trihemihydrate).

EXAMPLE 6

5-Ethoxy-3-spiro-[4-(2-carboxyethyloxy)cyclohexane]-1-[4-(N-tert-amylcarbamoyl)-2-methoxybenzenesulphonyl]-indolin-2-one.

(I): R$_1$=5-OC$_2$H$_5$; R$_2$=H; R$_3$=2-OCH$_3$; W =SO$_2$;

R$_4$ = 4-CONH—C(CH$_3$)$_2$—C$_2$H$_5$;  T—Z = —CH$_2$CH$_2$—COOH 1 g of chromium oxide is added at 0° C. to a mixture of 1.5 g of Compound (III A.2) obtained according to PREPARATION VI in 9 ml of acetic acid and 10 ml of water. The reaction mixture is stirred for two hours at 20° C., 80 ml of water are then added and, successively, extraction is carried out with ethyl acetate, the organic phases are dried over MgSO$_4$, the solvent is distilled and the expected product is isolated after chromatography on silica gel, elution being carried out with a 99/1 (v/v) dichloromethane/methanol mixture; M.p.=108° C. (hemihydrate).

EXAMPLE 7

5-Ethoxy-3-spiro-(4-ethoxycarbonylmethyloxycyclohexane)-1-[(4-N-tert-butylcarbamoyl-2-methoxy)benzenesulphonyl]indolin-2-one.

(I): R$_1$=5—OC$_2$H$_5$; R$_2$=H; R$_3$=2—OCH$_3$; W=SO$_2$; R$_4$=4—CONH-C(CH$_3$)$_3$; T-Z=—CH$_2$—COO—C$_2$H$_5$ 0.47 g of 2,6-di-tert-butylpyridine, 0.54 g of silver trifluoromethanesulphonate and then 0.27 ml of ethyl iodoacetate are added at 0° C. to a solution of 0.75 g of 5-ethoxy-3-spiro-(4-hydroxycyclohexane)-1-[4-(N-tert-butylcarbamoyl)-2-methoxybenzenesulphonyl]indolin-2-one (II.C1) in 30 ml of dichloromethane. The reaction mixture is stirred for 48 hours at 20° C. and then, successively, the reaction mixture is filtered, the solvent is evaporated and the expected product is isolated after chromatography on silica gel, elution being carried out with cyclohexane and then with a 20/80 (v/v) cyclohexane/dichloromethane mixture, and recrystallization from isopropanol; M.p.=165° C.

EXAMPLE 8

5-Ethoxy-3-spiro-(4-carboxymethyloxycyclohexane)-1-(4-N-tert-butylcarbamoyl-2-methoxybenzenesulphonyl)-indolin-2-one.

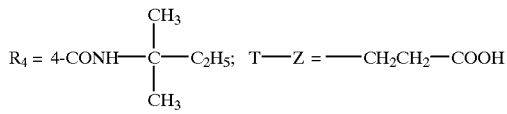

(I): R$_1$=5—OC$_2$H$_5$; R$_2$=H; R$_3$=2—OCH$_3$; W=SO$_2$; R$_4$=4—CONH-C(CH$_3$)$_3$; T-Z=—CH$_2$COOH 0.34 g of the product obtained in EXAMPLE 7 and 0.01 g of para-toluenesulphonic acid in 3 ml of benzyl alcohol are heated at 65° C. for 16 hours. The solvent is evaporated and then, successively, 1 ml of water and 1 ml of a saturated NaHCO$_3$ solution are added, extraction is carried out with ethyl acetate, the solvent is evaporated and then 5 ml of isopropanol, 0.25 g of 10% palladium-on-charcoal and 0.25 ml of cyclohexene are added. The reaction mixture is heated at 80° C. for 3 hours and then, successively, the reaction mixture is filtered, the catalyst is rinsed with methylene chloride, the solvents are evaporated and the expected product is isolated and purified by chromatography on silica gel, elution being carried out with a 98/2 (v/v) dichloromethane/methanol mixture. The fraction of the expected product is recrystallized from an 8/2 (v/v) isopropyl ether/ethyl acetate mixture; M.p.=175° C. (hemihydrate).

EXAMPLES 9 to 23 described in TABLE 1 below are prepared according to EXAMPLES 1 to 8 above.

TABLE 1

(I) [structure shown with R₁, W, R₄, T, Z substituents on spiro indolinone-cyclohexane core with N-phenyl bearing OCH₃ and R₄]

| Example Number | R₁ | W | R₄ | T | Z | Salt, Solvates (1) | M.p.; °C |
|---|---|---|---|---|---|---|---|
| 9 | —OC₂H₅ | SO₂ | —CONHC(CH₃)₃ | —(CH₂)₂— | N-methylpiperidin-4-ol | 1 H₂O | 170 |
| 10 | Cl | SO₂ | —OCH₃ | —(CH₂)₂— | morpholine | fumarate 1.5 H₂O | 88 |
| 11 | —OC₂H₅ | SO₂ | —CONHC(CH₃)₃ | —(CH₂)₂— | 1-methylpiperidine-4-COOC₂H₅ | fumarate 2 H₂O | 160 |
| 12 | —OC₂H₅ | SO₂ | —CONHC(CH₃)₃ | —(CH₂)₃— | morpholine | —(3) | 80 |
| 13 | —OC₂H₅ | SO₂ | —CONHC(CH₃)₃ | —(CH₂)₃— | morpholine | fumarate 2 H₂O | 170 |
| 14 | —OC₂H₅ | SO₂ | —CONHC(CH₃)₃ | —(CH₂)₂— | –N(CH₃)₂ | fumarate 1 H₂O | 150 |
| 15 | —OC₂H₅ | CH₂ | —CONHC(CH₃)₃ | —(CH₂)₂— | morpholine | fumarate 1 H₂O | 110 |
| 16 | —OC₂H₅ | SO₂ | —CONHC(CH₃)₃ | —(CH₂)₂— | 2,6-dimethylmorpholine | fumarate 1 H₂O | 165 |

TABLE 1-continued (I) Structure: spiro[indoline-cyclohexane] with R1 on indoline ring, N-W-phenyl (2-OCH3, 4-R4), cyclohexane bearing O-T-Z.

| Example Number | R₁ | W | R₄ | T | Z | Salt, Solvates (1) | M.p.; °C. |
|---|---|---|---|---|---|---|---|
| 17 | —OC₂H₅ | SO₂ | —CONHC(CH₃)₂CH₂CH₃ | —(CH₂)₂— | morpholin-4-yl | — | 65 |
| 18 | —OC₂H₅ | SO₂ | —CONHC(CH₃)₃ | —(CH₂)₂— | piperidin-1-yl | fumarate 1.5 H₂O | 190 |
| 19 | —OC₂H₅ | SO₂ | —CONHC(CH₃)₃ | —(CH₂)₂— | thiomorpholin-4-yl | fumarate 4 H₂O | 208 |
| 20 | —OC₂H₅ | SO₂ | —CONHC(CH₃)₃ | —(CH₂)₂— | —N(CH₃)(CH₂)₂OH | fumarate 1 H₂O (2) | 104 |
| 21 | —OC₂H₅ | SO₂ | —CONHC(CH₃)₃ | —(CH₂)₂— | —N(CH₃)(CH₂)₂OCH₃ | fumarate 1.5 H₂O | 100 |
| 22 | —OC₂H₅ | SO₂ | —CONHC(CH₃)₃ | —(CH₂)₂— | 4-methylpiperazin-1-yl | dioxolate 1 H₂O | 224 |
| 23 | —OC₂H₅ | SO₂ | —CONHC(CH₃)₃ | —(CH₂)₂— | —N(CH₂CH₂OCH₃)₂ | fumarate 1 H₂O | 98 |
| 24 | H | SO₂ | —CONHC(CH₃)₃ | —(CH₂)₃— | COOH | — | 183 |
| 25 | Cl | SO₂ | —CONHC(CH₃)₃ | —(CH₂)₃— | COOH | — | 163 |
| 26 | —OC₂H₅ | SO₂ | —CONHC(CH₃)₃ | —(CH₂)₃— | —NH—COOC(CH₃)₃ | H₂O | 114 |

TABLE 1-continued (I)

[Structure: spiro-indolin-2-one with R$_1$ on benzene ring, spirocyclohexane bearing O—T—Z substituent, N-substituted with W linker to a 2-methoxy-4-R$_4$-phenyl group]

| Example Number | R$_1$ | W | R$_4$ | T | Z | Salt, Solvates (1) | M.p.; °C. |
|---|---|---|---|---|---|---|---|
| 27 | —OC$_2$H$_5$ | SO$_2$ | —CONHC(CH$_3$)$_3$ | —(CH$_2$)$_2$— | 4-ethoxy-1-methylpiperidin-N-yl (N-Me, 4-OC$_2$H$_5$ piperidine) | HCl H$_2$O (4) | 150 |
| 28 | —OC$_2$H$_5$ | SO$_2$ | —COOCH$_2$C$_6$H$_5$ | —(CH$_2$)$_2$— | 1-methyl-4-hydroxypiperidin-N-yl | H$_2$O | 80 |
| 29 | —OC$_2$H$_5$ | SO$_2$ | —COOCH$_2$C$_6$H$_5$ | —(CH$_2$)$_2$— | 1-methyl-4-benzyloxypiperidin-N-yl | —(4) | 55 |
| 30 | —OCH$_2$C$_6$H$_5$ | SO$_2$ | —CONHC(CH$_3$)$_3$ | —(CH$_2$)$_2$ | N-methylmorpholin-N-yl | — | 62 |
| 31 | —OC$_2$H$_5$ | SO$_2$ | —CONHC(CH$_3$)$_3$ | —(CH$_2$)$_2$ | —N(CH$_2$C$_6$H$_5$)(CH$_2$)$_2$O(CH$_2$)$_2$OH | (5) | 69 |

(1): The most polar isomers, except when otherwise indicated
(2): Mixture of isomers
(3): The least polar isomer
(4): The 4-hydroxypiperidine ethers are obtained by alkylation of the N-tert-butyloxycarbonyl-4-hydroxy-piperidine and of the corresponding halide in the presence of sodium hydride followed by an acid hydrolysis of the tert-butyloxycarbonyl group.
(5): The 2-(2-(N-benzylamino)ethoxy)ethanol was prepared by reducing amination by sodium borohydride of the imine issued from 2-(2-aminoethoxy)ethanol and benzaldehyde, in methanol and at 0° C.

EXAMPLE 32

5-Ethoxy-3-spiro-[4-(2-(2-hydroxyethylamino)-ethyloxy)cyclohexane]-1-[4-(4-N-tert-butylcarbamoyl)-2-methoxybenzenesulfonyl]indolin-2-one (polar isomer).

(I): R₁=5—OC₂H₅; R₂=H; R₃=2—OCH₃; W=SO₂; R₄=4—CONH-C(CH₃)₃; T-Z=CH₂CH₂NHCH₂CH₂OH;

a) 0.33 g of benzyloxyacetaldehyde and then 0.46 g of sodium triacetoxyborohydride are added to a solution of 0.9 g of the amine hydrochloride of EXAMPLE 4 (polar isomer) in 8 ml of tetrahydrofurane, cooled to 5° C. The reaction mixture is stirred at 20° C. for 3 hours, 10 ml of 1N HCl are added, extraction is carried out with ethyl acetate, the organic phase is washed with a saturated NaCl solution, dried over MgSO4 and the solvent is evaporated under reduced pressure. The residue is chromatographed on a silica gel column, elution being carried out with a 98/2 (v/v) dichloromethane/methanol mixture.

b) 0.4 ml of 1,4-cyclohexadiene, 0.3 g of (10%) Palladium/C are added to the benzyl ether previously obtained, dissolved in 5 ml of glacial acetic acid and are heated at 60° C. under nitrogen bubbling for 16 hours according to the method described in J. Org. Chem. 43, 21 (1978).

The catalyst is filtered off, 10 ml of water are added to the reaction mixture, which is neutralized with a saturated NaHCO₃ solution; the extraction is carried out with ethyl acetate, washing is carried out with water, drying is effected over MgSO₄ and the solvent is evaporated under reduced pressure. The residue is chromatographed on a silica gel column, elution being carried out with a 98/2 (v/v) dichloromethane/methanol mixture. The expected product is isolated in the form of hydrate hydrochloride by preparing the hydrochloride with a hydrochloric isopropanol solution and cristallization from diethyl ether, M.p.=130° C.

EXAMPLE 33

5-Ethoxy-3-spiro-[4-(2-(2-hydroxyethyloxy)-ethylamino)ethyloxy)cyclohexane]-1-[4-(4-N-tert-butylcarbamoyl)-2-methoxybenzenesulfonyl]indolin-2-one.

The expected compound in the form of the trihemihydrated hydrochloride is isolated by debenzylation of the compound of EXAMPLE 31 according to the procedure described in EXAMPLE 32b) in ethanol and by preparing the hydrochloride in ethyl ether; M.p.=159° C.

EXAMPLE 34

5-Ethoxy-3-spiro-[4-(2-(4-benzyloxypiperidino)-ethyloxy)cyclohexane]-1-[4-carboxy-2-methoxybenzenesulfonyl]indolin-2-one.

(I): R₁=5—OC₂H₅; R₂=H; R₃=2—OCH₃; W=SO₂;

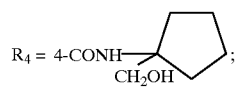

(prepared by selective debenzylation according to Tetrah. Letters, 1986, 3753).

0.62 ml of tert-butyldimethylsilane and 0.06 ml of triethylamine are added to 0.03 g of Palladium acetate solution in 4 ml of dichloromethane and the reaction medium is stirred for 15 minutes at 20° C. A solution of 1 g of the compound described in EXAMPLE 29 in 2.6 ml of dichloromethane is added slowly and stirring is carried out for 4 hours at 20° C. 1 ml of acetic acid is added, followed by filtration, rinsing with dichloromethane and the filtrate is washed with an aqueous ammonium chloride solution and then with water. The expected product is isolated after evaporation of the solvent, cristallization from pentane and drying at 50° C. under vacuum for 5 hours; M.p.=120° C.

EXAMPLE 35

5-Ethoxy-3-spiro-[4-(2-(4-benzyloxypiperidino)-ethyloxy)cyclohexane]-1-[4-(N-(1-hydroxymethyl)cyclopentylcarbamoyl-2-methoxybenzenesulfonyl]indolin-2-one.

(I): R₁=5—OC₂H₅; R₂=H; R₃=2—OCH₃; W=SO₂;

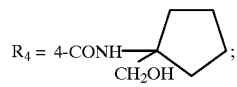

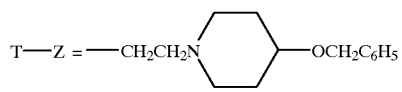

1.27 g of oxalyl chloride are added to a suspension of 0.7 g of the compound prepared in EXAMPLE 34 in 7 ml of toluene and 2.5 ml of dichloromethane and the reaction mixture is stirred for 6 hours at 20° C. The solvents are evaporated, the residue is dried for 2 hours at 20° C. under vacuum and is dissolved in 20 ml of toluene then this solution is added to a solution cooled to about −40° C. of 1.16 g of 1-amino-1-cyclopentane-methanol in 30 ml of toluene. The reaction mixture is stirred for 2 hours at 20° C., 30 ml of water and 100 ml of ethyl acetate are added. The organic phase is dried over Na₂SO₄ and evaporated under reduced pressure. The expected product is isolated after chromatography on silica gel, elution being carried out with a 95/5 (v/v) dichloromethane/methanol mixture; M.p.=103° C.

EXAMPLE 36

5-Ethoxy-3-spiro-[4-(2-(4-hydroxypiperidino)-ethyloxy)cyclohexane]-1-[4-(N-(1-hydroxymethyl)cyclopentylcarbamoyl-2-methoxybenzenesulfonyl]indolin-2-one.

(I): R₁=5—OC₂H₅; R₂=H; R₃=2—OCH₃; W=SO₂;

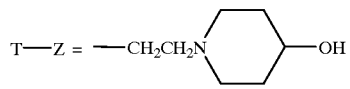

The expected product is isolated in the form of a hydrated base, according to the procedure described in EXAMPLE 32 b) starting from EXAMPLE 35, after chromatography on a silica gel column, elution being carried out with a 92/8 (v/v) dichloromethane/methanol mixture; M.p.=109° C.

EXAMPLE 37

5-Ethoxy-3-spiro-[4-(2-(benzyloxycarbonylmethyl-amino)ethyloxy)cyclohexane]-1-[4-(4-N-tert-butylcarbamoyl)-2-methoxybenzenesuphonyl]indolin-2-one.

(I): $R_1$=5—$OC_2H_5$; $R_2$=H; $R_3$=2—$OCH_3$; W=$SO_2$; $R_4$=4—CONH-C(CH$_3$)$_3$; T-Z=—CH$_2$CH$_2$NHCH$_2$COOCH$_2$C$_6$H$_5$

A residue is isolated according to the procedure described in EXAMPLE 5 starting from the compound (II B.2) and the 2-methoxy-4(N-tert-butylcarbamoyl)benzenesuphonyl chloride, and stirred for 2 hours at 20° C. in 3 ml of a ethyl acetate solution which is saturated with gaseous hydrochloric acid. The expected product is obtained after alkalinization and chromatography on silica gel, elution being carried out with an 8/2 (v/v) cyclohexane/ethyl acetate mixture; the monohydrated hydrochloride melts at 160° C.

EXAMPLE 38

5-Ethoxy-3-spiro-[4-(2-(carboxymethylamino)ethyloxy)-cyclohexane]-1-[4-(4-N-tert-butylcarbamoyl)-2-methoxybenzenesulfonyl]indolin-2-one.

(I): $R_1$=5—$OC_2H_5$; $R_2$=H; $R_3$=2—$OCH_3$; W=$SO_2$; $R_4$=4—CONH-C(CH$_3$)$_3$; T-Z=—CH$_2$CH$_2$NHCH$_2$COOH 0.06 g of the compound of EXAMPLE 37, 6 g of cyclohexene, 0.05 g of 10% Palladium/charcoal in 10 ml of ethanol are heated to reflux for 1 hour 30, the catalyst is filtered off and the solvent is evaporated under reduced pressure. The expected product is isolated in a dihydrated form after chromatography on silica gel, elution being carried out with a 90/10 (v/v) dichloromethane/methanol mixture; M.p.=199° C.

EXAMPLE 39

5-Hydroxy-1-[4-(N-tert-butylcarbamoyl)-2-methoxybenzenesulfonyl]-3-spiro-[4-(2-morpholinoethyloxy)cyclohexane]indolin-2-one. (mixture of isomers)

(I): $R_1$=5—OH; $R_2$=H; $R_3$=2—$OCH_3$; W=$SO_2$;

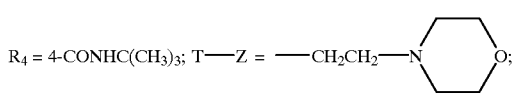

The expected product is isolated in a hydrated form according to the procedure described in EXAMPLE 38 starting from the compound of EXAMPLE 30; M.p.=125° C.

EXAMPLE 40

5-Ethoxy-1-[4-(N-tert-butylcarbamoyl)-2-methoxybenzenesulfonyl]-3-spiro-[4-(2-N-oxide morpholinoethyloxy)-cyclohexane]indolin-2-one.

(I): $R_1$=5—$OC_2H_5$; $R_2$=H; $R_3$=2—$OCH_3$; W=$SO_2$;

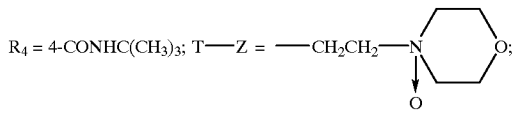

0.8 ml of 30% hydrogen peroxide is added to 0.5 g of the compound described in EXAMPLE 2 dissolved in 10 ml of methanol and the reaction mixture is heated to 45° C. for 16 hours. The solvent is evaporated under reduced pressure and the residue is chromatographed on silica gel, elution being carried out with an 85/15 (v/v) dichloromethane/methanol mixture. The expected product is isolated in a hemihydrated form after recristallization from a 40/60 (v/v) cyclohexane/ethyl acetate mixture; M.p.=189° C.

EXAMPLE 41

Methylsulfate of 5-Ethoxy-1-[4-(N-tert-butylcarbamoyl)-2-methoxybenzenesulfonyl]-3-spiro-[4-(2-N-methylmorpholiniumethyloxy)cyclohexane]indolin-2-one.

(I): $R_1$=5—$OC_2H_5$; $R_2$=H; $R_3$=2—$OCH_3$; W=$SO_2$;

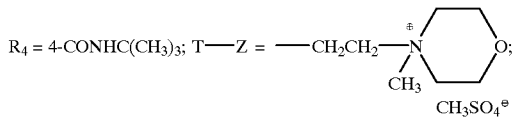

0.05 ml of dimethylsulphate is added to 0.25 g of the compound described in EXAMPLE 2 dissolved in 2.5 ml of acetonitrile and the reaction mixture is heated at 60° C. for 24 hours. The solvent is evaporated and the expected product is isolated in a hemihydrated form after cristallization from diethyl ether and drying at 40° C. under vacuum for 5 hours; M.p.=190° C.

EXAMPLE 42

5-Ethoxy-3-spiro-[4-(2-(2-(N-tert-butoxycarbonylglycyl)amino)ethyloxy)cyclohexane]-1-[4-(4-N-tert-butylcarbamoyl)-2-methoxybenzenesulfonyl]indolin-2-one.

(I): $R_1$=5—$OC_2H_5$; $R_2$=H; $R_3$=2—$OCH_3$; W=$SO_2$; $R_4$=4—CONH-C(CH$_3$)$_3$; T-Z=—CH$_2$CH$_2$—NHCOCH$_2$NHCOOC(CH$_3$)$_3$ 0.28 g of benzotriazol-1-yl-oxy-tris(dimethylamino)-phosphonium hexafluorophosphate and 0.24 ml of triethylamine and then 0.35 g of the hydrochloride of the compound of EXAMPLE 4 (polar isomer) are added at 5° C. to a solution of 0.11 g of N-α-tert-butyloxycarbonylglycine in 2 ml of acetonitrile and stirring is carried out at about 20° C. for 4 hours.

The solvent is evaporated under reduced pressure, the residue is taken up with ethyl acetate, washed successively with a KHSO$_4$/K$_2$SO$_4$ buffer solution of pH=2, with water, with a saturated NaHCO$_3$ solution and then with water. The organic phase is dried over MgSO$_4$ and the solvent is evaporated under reduced pressure and the residue is chromatographed on a silica gel column, elution being carried out with a 99/1 (v/v) dichloromethane/methanol mixture. The expected product is isolated; M.p.=158° C.

EXAMPLE 43

5-Chloro-3-spiro-[4-(N-(3-dimethylaminopropyl)-carbamoylmethoxy)cyclohexane]-1-[4-(4-N-tert-butylcarbamoyl)-2-methoxybenzenesulfonyl]indolin-2-one.

(I): $R_1$=5—Cl; $R_2$=H; $R_3$=2—$OCH_3$; W=$SO_2$; $R_4$=4—CONH-C($CH_3$)$_3$; T-Z=—$CH_2$CONH($CH_2$)$_3$N($CH_3$)$_2$

The expected product is isolated in a monohydrated hydrochloride form according to the procedure described in EXAMPLE 42 and starting from the carboxylic acid of EXAMPLE 25 and 3-dimethylaminopropanamine; M.p.=135° C.

The compounds 44 to 50 collated in Table 2 below are prepared according to the procedures of EXAMPLES 42 and 43 by reacting amines or acids appropriately selected.

of the compound of EXAMPLE 42 in 3 ml of ethyl acetate and the reaction mixture is stirred for 2 hours at room temperature. The solvent is evaporated, cristallization is carried out from diethyl ether, drying is carried out under vacuum to obtain the expected product in the form of a dihydrated hydrochloride; M.p.=169° C.

EXAMPLE 52

5-Ethoxy-3-spiro-[4-(2-(4-carboxybutyramido)ethyloxy)cyclohexane]-1-[4-(4-N-tert-butylcarbamoyl)-2-methoxybenzenesulfonyl]indolin-2-one.

(I): $R_1$=5—$OC_2H_5$; $R_2$=H; $R_3$=2—$OCH_3$; W=$SO_2$; $R_4$=4—CONH-C($CH_3$)$_3$; T-Z=—$CH_2CH_2$NHCO($CH_2$)$_3$COOH

The expected product is isolated from the compound of EXAMPLE 45 and according to the procedure of

TABLE 2

(I)

[Structure: spiro indolin-2-one with $R_1$ on benzene ring, cyclohexane bearing O—T—Z, N-sulfonyl group with 2-methoxy-4-CONHC($CH_3$)$_3$ benzene]

| Example Number | $R_1$ | T | Z | Salt Solvate (1) | M.p.; ° C. |
|---|---|---|---|---|---|
| 44 | 5-$OC_2H_5$ | —($CH_2$)$_2$— | —NHCO($CH_2$)$_3$N($CH_3$)$_2$ | HCl | 151 |
| 45 | 5-$OC_2H_5$ | —($CH_2$)$_2$— | —NHCO($CH_2$)$_3$COO$CH_3$ | — | 138 |
| 46 | 5-$OC_2H_5$ | —($CH_2$)$_2$— | —NHCO$CH_2$N($CH_3$)$_2$ | HCl $H_2O$ | 144 |
| 47 | 5-$OC_2H_5$ | —($CH_2$)$_2$— | —NHCO($CH_2$)$_2$O$CH_3$ | 1$H_2O$ | 108 |
| 48 | 5-$OC_2H_5$ | —($CH_2$)$_2$— | —NHCO($CH_2$)$_2$CH(NHCOOC($CH_3$)$_3$)COOC($CH_3$)$_3$ | (4) $H_2O$ | 133 |
| 49 | 5-$OC_2H_5$ | —($CH_2$)$_2$— | —NHCOCH(NHCOOC$H_2C_6H_5$)($CH_2$)$_2$COO$CH_2C_6H_5$ | (5) | 108 |
| 50 | H | $CH_2$ | —CONH($CH_2$)$_2$OH | 0.5 $H_2O$ | 183 |

(4) starting from tert-butyl N-α-tert-butyloxyglutamate in natural configuration.

(5) from the γ-benzylic ester of N-α-benzyloxycarbonylglutamic acid in natural configuration.

EXAMPLE 51

5-Ethoxy-3-spiro-[4-(2-glycylaminoethyloxy)-cyclohexane]-1-[4-(4-N-tert-butylcarbamoyl)-2-methoxybenzenesulfonyl]indolin-2-one.

(I): $R_1$=5—$OC_2H_5$; $R_2$=H; $R_3$=2—$OCH_3$; W=$SO_2$; $R_4$=4—CONH-C($CH_3$)$_3$; T-Z=—$CH_2CH_2$NHCO$CH_2$$NH_2$ 3 ml of a saturated solution of gaseous hydrochloric acid in ethyl acetate are added at 5° C. to a suspension of 0.3 g EXAMPLE 8 by transesterification with benzylic alcohol followed by hydrogenolysis. M.p.=117° C.

EXAMPLE 53

5-Ethoxy-3-spiro-[4-(2-L-γ-glutamylamino)ethyloxy)-cyclohexane]-1-[4-(4-N-tert-butylcarbamoyl)-2-methoxybenzenesulfonyl]indolin-2-one.

(I): $R_1$=5—$OC_2H_5$; $R_2$=H; $R_3$=2—$OCH_3$; W=$SO_2$; $R_4$=4—CONH-C($CH_3$)$_3$; T-Z=—$CH_2CH_2$NHCO$CH_2CH_2$CH($NH_2$)COOH

The expected product is isolated in the form of a hydrochloride operating according to the procedure described in EXAMPLE 51 starting from the compound of EXAMPLE 48; M.p.=230° C.

EXAMPLE 54

5-Ethoxy-3-spiro-[4-(2-L-pyroglutamylamino)ethyloxy)-cyclohexane]-1-[4-(4-N-tert-butylcarbamoyl)-2-methoxybenzenesulfonyl]indolin-2-one.

(I): $R_1=5$—$OC_2H_5$; $R_2=H$; $R_3=2$—$OCH_3$; $W=SO_2$;

$R_4 = 4$-$CONHC(CH_3)_3$; T—Z = —$CH_2CH_2NHCO$ 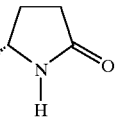

A mixture of 0.245 g of the compound of EXAMPLE 49, 0.5 ml of cyclohexadiene and 0.25 g of 10% Palladium/charcoal in 2 ml of ethyl acetate is heated at 80° C. The catalyst is separared by filtration, evaporation is carried out under reduced pressure and the residue is taken up with ethyl acetate and washed with a saturated sodium bicarbonate. The solvent is evaporated under reduced pressure and the residue is chromatographed on a silica gel column, elution being carried out with a 98/2 (v/v) dichloromethane/methanol mixture. The resulting residue is taken up with diethyl ether; M.p.=171° C.

We claim:

1. Compound of formula

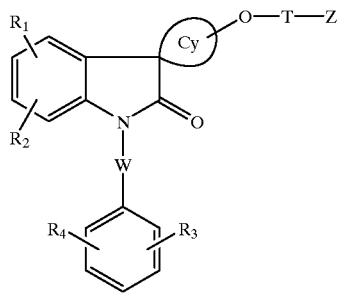

(I)

in which:

$R_1$ and $R_2$ each independently represent a hydrogen; a hydroxyl; a halogen; a $(C_1-C_7)$alkyl; a $(C_1-C_7)$polyfluoroalkyl; a $(C_1-C_7)$alkoxy; a $(C_1-C_7)$-alkylthio; a $(C_1-C_7)$polyfluoroalkoxy; a $(C_3-C_7)$cycloalkyloxy; a $(C_3-C_7)$cycloalkylthio; a cycloalkylmethoxy or a cycloalkyl-methylthio in which the cycloalkyl is $C_3-C_7$; a phenoxy; a benzyloxy; a nitro; or a cyano;

$R_3$ and $R_4$, each independently of one another, substitute the phenyl group one or a number of times and represent a hydrogen; a halogen; a $(C_1-C_7)$alkyl; a $(C_2-C_7)$alkenyl; a $(C_1-C_7)$polyhaloalkyl; a phenyl or a benzyl; a cyano; a nitro; an —$NR_5R_6$ group; a hydroxyamino; a hydroxyl; an $OR_7$ group; an $SR_7$ group; a —$COOR_8$ group, a —$CONR_9R_{10}$ group; or a —$CSNR_9R_{10}$ group, at least one of the $R_3$ and $R_4$ radicals being other than hydrogen;

$R_5$ and $R_6$ each independently represent a hydrogen; a $(C_1-C_7)$alkyl; a $(C_2-C_7)$alkenyl; a phenyl; a benzyl; a $(C_1-C_7)$alkylcarbonyl; a $(C_1-C_7)$alkylthiocarbonyl; a $(C_3-C_7)$cycloalkylcarbonyl; a $(C_3-C_7)$cycloalkylthiocarbonyl; a benzoyl; a thienylcarbonyl; a furylcarbonyl; a $(C_1-C_7)$alkyloxycarbonyl; a phenoxycarbonyl; a benzyloxy-carbonyl; a carbamoyl or a thiocarbamoyl which is unsubstituted or substituted by $R_9$ and $R_{10}$ or alternatively $R_5$ and $R_6$ form, with the nitrogen atom to which they are bonded, a heterocyclic group chosen from the pyrrolidine, pyrroline, pyrrole, indoline, indole and piperidine groups;

$R_7$ represents a $(C_1-C_7)$alkyl; a $(C_2-C_7)$alkenyl; a phenyl; a benzyl; a $(C_3-C_7)$cycloalkyl; a $(C_1-C_7)$polyfluoroalkyl; a formyl; a $(C_1-C_7)$alkylcarbonyl; a benzoyl; or a benzylcarbonyl;

$R_8$ represents a hydrogen; a $(C_1-C_7)$alkyl; a phenyl; or a benzyl;

$R_9$ and $R_{10}$ each independently represent hydrogen; a $(C_1-C_7)$alkyl; a $(C_1-C_7)$polyfluoroalkyl; a $(C_2-C_7)$alkenyl; a $(C_3-C_7)$cycloalkyl optionally substituted by a hydroxy $(C_1-C_4)$alkyl; a pyridyl; a phenyl; a thienyl; a furyl; or alternatively $R_9$ and $R_{10}$ form, with the nitrogen atom to which they are bonded, a heterocyclic group chosen from the pyrrolidine, piperidine and piperazine groups, which is unsubstituted or substituted by $(C_1-C_4)$alkyls; and the $(C_4-C_7)$azacycloalkyl groups;

W represents a —$CH_2$— or —$SO_2$— group;

Cy forms, with the carbon to which it is bonded, a non-aromatic, saturated or unsaturated $C_3-C_{12}$ hydrocarbon ring which is optionally condensed or substituted by one or a number of $(C_1-C_7)$alkyl groups, it being possible for the said groups to substitute the same carbon atom one or a number of times, or by a $C_3-C_6$ spirocycloalkyl;

T represents a $(C_1-C_4)$alkylene which is optionally interrupted by a $(C_3-C_6)$cycloalkylene, the said alkylenes optionally being substituted one or a number of times on the same carbon atom by a $(C_1-C_3)$alkyl; or alternatively T represents a direct bond;

Z represents an —$NR_{11}R_{12}$ group; —$^+NR_{11}R_{12}(C_1-C_4)$-alkyl (A$^-$), (A$^-$) being an anion; —$N(O)R_{11}R_{12}$; a —$COOR_{11}$ group; an —$NR_{11}COR_{12}$ group; a benzyloxycarbonylamino; a —$CONR_{11}R_{12}$ group; it being understood that when T represents a methylene or a direct bond, Z cannot be —$NR_{11}R_{12}$; —$^+NR_{11}R_{12}(C_1-C_4)$alkyl; —$N(O)R_{11}R_{12}$; —$NR_{11}COR_{12}$; a benzyloxycarbonylamino;

$R_{11}$ and $R_{12}$ each independently represent a hydrogen; a $(C_1-C_7)$alkyl; a $(C_1-C_4)$alkoxy; a $(C_3-C_7)$cycloalkyl; a phenyl; a $(C_1-C_3)$alkylenecycloalkyl, in which the cycloalkyl is $C_3-C_7$, or a $(C_1-C_3)$alkylenephenyl, it being possible for the said groups optionally to be mono- or polysubstituted by $R_{13}$;

or alternatively $R_{11}$ and $R_{12}$ optionally form, with the nitrogen atom to which they are bonded, a heterocycle chosen from azetidine, pyrrolidine, piperidine, piperazine, piperazinone, morpholine, morpholinone, thiomorpholine and hexahydroazepine heterocycles, which heterocycle is optionally mono- or polysubstituted by $R_{13}$; or a thiomorpholine 1,1-dioxide or a thiomorpholine 1-oxide; or alternatively $R_{12}$ represents a pyrrolidone or a piperidone;

$R_{13}$ represents a hydroxyl group; a $(C_1-C_4)$alkyl; a $(C_1-C_4)$alkoxy; a mercapto; a $(C_1-C_4)$alkylthio; a $(C_1-C_4)$-alkylsulphinyl; a $(C_1-C_4)$alkylsulphonyl; a benzyloxy; a hydroxyalkyloxy; an —$NR_{14}R_{15}$ group in which $R_{14}$ and $R_{15}$ each independently represent hydrogen or a $(C_1-C_4)$alkyl or a $(C_1-C_4)$alkyloxycarbonyl or a benzyloxycarbonyl; a carboxyl; a $(C_1-C_4)$ alkyloxycarbonyl, a phenoxycarbonyl, a benzyloxycarbonyl; a carbamoyl; an amidino; a guanidino; an imidazolyl; a thienyl; a pyridyl; an indolyl; or a tetrahydroisoquinolyl;

the phenyl group, which is constituent of the $R_1$, $R_2$, $R_3$, $R_4$, $R_5$, $R_6$, $R_7$, $R_8$, $R_9$, $R_{10}$, $R_{11}$ and $R_{12}$ substituents, being unsubstituted, mono- or di-substituted by a $(C_1-C_7)$alkyl, a $(C_1-C_7)$alkoxy, a tri-fluoromethyl, a halogen or trisubstituted by a $(C_1-C_7)$-alkyl, a $(C_1-C_7)$ alkoxy or a halogen; and its salts.

2. Compound according to claim 1 of formula:

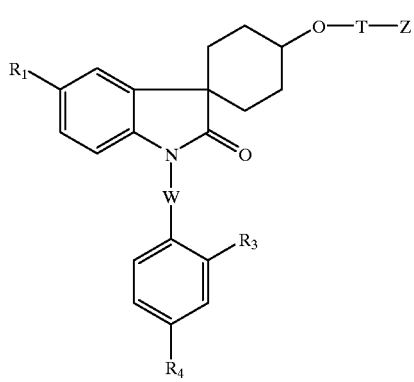

(I.1)

in which $R_1$, $R_3$, $R_4$, W, T and Z are as defined for (I) in claim 1 or one of its salts, solvates or hydrates.

3. Compound according to claim 1 of formula:

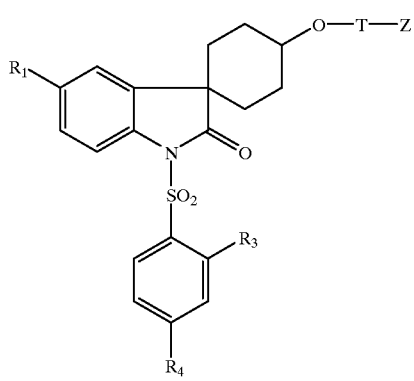

(I.2)

in which $R_1$, $R_3$, $R_4$, T and Z are as defined for (I) in claim 1 or one of its salts, solvates or hydrates.

4. Compound according to claim 1 of formula:

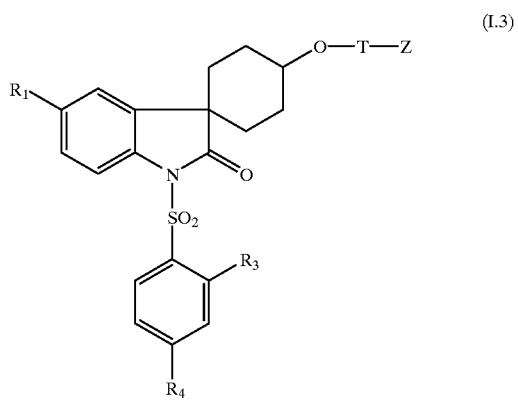

(I.3)

in which $R_1$, $R_3$ and $R_4$ are as defined for (I) in claim 1, T represents a $(C_1-C_3)$alkylene and Z represents an amino group, a 2-hydroxyethylamino, a 2-(2-hydroxy) ethyloxyethylamino, a morpholinyl or a carboxylic acid, and its salts, solvates or hydrates.

5. Compound according to claim 1 of formula:

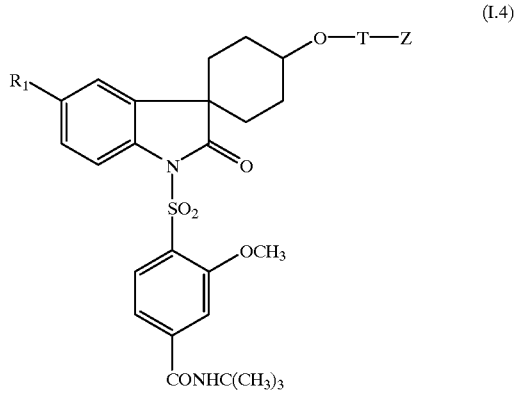

(I.4)

in which $R_1$, T and Z are as defined for (I) in claim 1 or one of its salts, solvates or hydrates.

6. Compound according to claim 1, wherein it is one of the compounds below:
 5-chloro-3-spiro-[4-(2-morpholinoethyloxy) cyclohexane]-1-[4-(N-tert-butylcarbamoyl)-2-methoxybenzene-sulphonyl]indolin-2-one;
 5-ethoxy-3-spiro-[4-(2-aminoethyloxy)cyclohexane]-1-[4-(4N-tert-butylcarbamoyl)-2-methoxybenzene-sulphonyl]indolin-2-one;
 5-ethoxy-3-spiro-[4-(2-(N-methyl-N-(2-hydroxy-ethyl) amino)ethyloxy)-cyclohexane]-1-[4-(N-tert-butylcarbamoyl)-2-methoxybenzenesulphonyl]indolin-2-one;
 5-ethoxy-3-spiro-[4-(2-morpholinoethyloxy)cyclohexane]-1-[4(N-tert-butylcarbamoyl)-2-methoxybenzyl]-indolin-2-one;
 5-ethoxy-1-[4-(N-tert-butylcarbamoyl)-2-methoxybenzenesulphonyl]-3-spiro-[4(2-morpholinoethyloxy)-cyclohexane]indolin-2-one;
 5-ethoxy-3-spiro-(4-carboxymethyloxycyclohexane)-1-(4-N-tert-butylcarbamoyl-2-methoxybenzenesulphonyl)-indolin-2-one;
 5-ethoxy-3-spiro-[4-(2-morpholinoethyloxy)cyclohexane]-1-[4-(N-tert-amylcarbamoyl)-2-methoxybenzenesulphonyl]indolin-2-one;

5-ethoxy-3-spiro-[4(2-carboxyethyloxy cyclo-hexane]1-[4-(N-tert-amylcarbamoyl)-2-methoxybenzene-sulphonyl]indolin-2-one;

5-ethoxy-1-[4-(N',N'-diethylureido)-2-methoxy-benzenesulphonyl]-3-spiro-[4-(2-dimethylaminoethyloxy)-cyclohexane]indolin2-one;

5-Ethoxy-3-spiro-[(2-(4-ethoxypiperidino)-ethyloxy)cyclohexane]-1-[4-(N-tert-butylcarbamoyl)-2-methoxybenzenesulfonyl]indolin-2-one;

5-Ethoxy-3-spiro-[4-(2-glycylaminoethyloxy)-cyclohexane]-1-[4-(N-tert-butylcarbamoyl)-2-methoxy-benzenesulfonyl]indolin-2-one;

5-Ethoxy-3-spiro-[4-(2-(N,N-dimethylglycylamino)-ethyloxy)cyclohexane]-1-[4-(N-tert-butylcarbamoyl)-2-methoxybenzenesulfonyl]indolin-2-one;

5-Chloro-3-spiro-[4-(N-(3-dimethylaminopropyl)-carbamoylmethyloxy)-cyclohexane]-1-[4(N-tert-butylcarbamoyl)-2-methoxybenzenesulfonyl]indolin-2-one;

5-Ethoxy-3-spiro-[4-(2-(4-dimethylaminobutyryl-amino)ethyloxy)cyclohexane]-1-[4-(N-tert-butylcarbamoyl)-2-methoxybenzenesulfonyl]indolin-2-one;

5-Ethoxy-3-spiro-[4(2-(2-hydroxyethylamino)-ethyloxy)cyclohexane]-1-[4-(N-tert-butylcarbamoyl)-2-methoxybenzenesulfonyl]indolin-2-one;

5-Ethoxy-3-spiro-[4-2-(-L-γ-glutamylamino)-ethyloxy)cyclohexane]-1-[4-(N-tert-butylcarbamoyl)-2-methoxybenzenesulfonyl]indolin-2-one;

5-Ethoxy-3-spiro-[4-(2-(-L-pyroglutamylamino)-ethyloxy)cyclohexane]-1-[4-(N-tert-butylcarbamoyl)-2-methoxybenzenesulfonyl]indolin-2-one;

5-Ethoxy-3-spiro-[4-(2-(2-(2-hydroxyethyloxy)-ethylamino)ethyloxy)-cyclohexane]-1-[4-(N-tert-butylcarbamoyl)-2-methoxybenzenesulfonyl]indolin-2-one;

or their pharmaceutically acceptable salts, solvates or hydrates.

7. Process for the preparation of a compound of formula (I) according to claim 1, wherein:

(1) either when $Z=NR_{11}R_{12}$, in which R11 and R12 are as defined for (1):

(1a) when at least one of the $R_{11}$ and $R_{12}$ radicals is different from hydrogen, a compound of formula:

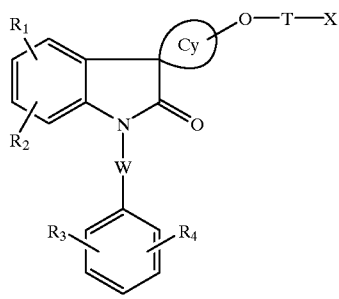

(II A)

in which $R_1$, $R_2$, $R_3$, $R_4$, W, Cy and T are as defined for (I) and in which X is a halogen or a sulphonic acid derivative is reacted with a derivative of formula ZH in a solvent selected from dimethylformamide, tetrahydrofuran or acetonitrile, at temperatures of between 0° and 120° C.;

(1b) when $R_{11}$ and $R_{12}=H$, the compound (IA), in which X is an azido, is reduced to amino;

(2) or, when Z=—COOH, a compound of formula:

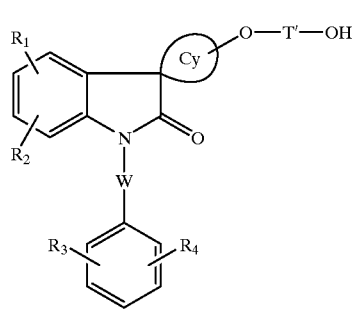

(II' A)

in which $R_1$, $R_2$, W, $R_3$, $R_4$ and Cy are as defined for (I) and T' represents T—$CH_2$—, is oxidized in an acid solvent at a temperature of between 0° C. and 100° C., alkali metal dichromates or alkali metal or alkaline-earth metal permanganates;

(3) or a compound of formula:

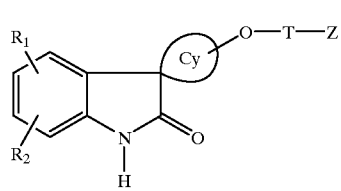

(II B)

in which $R_1$, $R_2$, Cy, T and Z are as defined for (I), is reacted with a compound of formula:

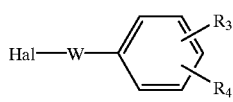

(2)

in which W, $R_3$ and $R_4$ are as defined for (I) and Hal represents a halogen atom, in an anhydrous solvent in the presence of a metal hydride or an alkali metal alkoxide at temperatures of between −40° and 25° C.;

(4) or, when Z=—COOH, a compound of formula:

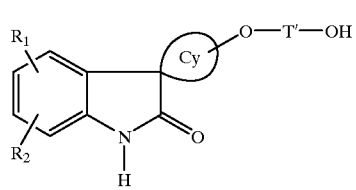

(II' B)

in which $R_1$, $R_2$ and Cy are as defined above for (I) and T' represents T—$CH_2$, is oxidized, then the acid thus obtained of formula:

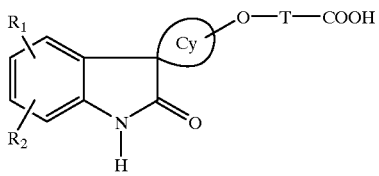

(II″ B)

in which $R_1$, $R_2$, Cy and T are as defined above for (I), is subsequently optionally protected by a protective group for the carboxylic acid, in order to obtain the intermediate of formula:

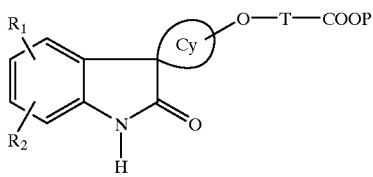

(II″ BP)

in which $R_1$, $R_2$, Cy and T are as defined for (I) and P represents a protective group chosen from an alkyl, a tert-butyl or a benzyl, and, finally, this compound (II″BP) is subjected to the action of a derivative of formula (2) in order to obtain, after deprotection, a compound (I); one of its quaternary ammoniums, oxides, sulphones or salts.

8. Pharmaceutical composition containing, as active principle, a compound of formula (I) according to claim 1 or one of its pharmaceutically acceptable salts, hydrates or solvates.

9. Pharmaceutical composition containing, as active principle, a compound of formula (I1.) according to claim 2 or one of its pharmaceutically acceptable salts, hydrates or solvates.

10. Pharmaceutical composition containing, as active principle, a compound of formula (I.2) according to claim 3 or one of its pharmaceutically acceptable salts, hydrates or solvates.

11. Pharmaceutical composition containing, as active principle, a compound of formula (I.3) according to claim 4 or one of its pharmaceutically acceptable salts, hydrates or solvates.

12. Pharmaceutical composition containing, as active principle, a compound of formula (I.4) according to claim 5 or one of its pharmaceutically acceptable salts, hydrates or solvates.

13. Pharmaceutical composition containing, as active principle, a compound according to claim 6.

14. Pharmaceutical composition according to claim 8 also containing another active principle.

15. Pharmaceutical composition according to claim 14, characterized in that the other active principle is a specific antagonist of the angiotensin II receptor.

16. Pharmaceutical composition according to claim 15, characterized in that the specific antagonist of the angiotensin II receptor is irbesartan.

17. Pharmaceutical composition containing a combination of 5ethoxy-1-[4(N-tert-butylcarbamoyl)-2-methoxybenzene-sulphonyl]-3spiro-[(2-morpholinoethyloxy)cyclohexane]-indolin-2-one and irbesartan.

18. A method for the treatment of diseases in which the vasopressin and/or oxytocin receptor is involved which comprises administering to a patient in need of such treatment an effective amount of a compound according to claim 1.

19. A method for the treatment of diseases in which the vasopressin and/or oxytocin receptor is involved which comprises administering to a patient in need of such treatment an effective amount of a compound according to claim 2.

20. A method for the treatment of diseases in which the vasopressin and/or oxytocin receptor is involved which comprises administering to a patient in need of such treatment an effective amount of a compound according to claim 3.

21. A method for the treatment of diseases in which the vasopressin and/or oxytocin receptor is involved which comprises administering to a patient in need of such treatment an effective amount of a compound according to claim 4.

22. A method for the treatment of diseases in which the vasopressin and/or oxytocin receptor is involved which comprises administering to a patient in need of such treatment an effective amount of a compound according to claim 5.

23. A method for the treatment of diseases in which the vasopressin and/or oxytocin receptor is involved which comprises administering to a patient in need of such treatment an effective amount of a compound according to claim 6.

* * * * *

UNITED STATES PATENT AND TRADEMARK OFFICE
CERTIFICATE OF CORRECTION

PATENT NO. : 5,994,350
DATED : November 30, 1999
INVENTOR(S) : Loic Foulon, Georges Garcia, Claudine Serradeil-Le Gal and Gerard Valette It is certified that error appears in the above-identified patent and that said Letters Patent is hereby corrected as shown below:

Column 6, line 7 to Column 7,
Line 4, should be deleted as this is a duplicate of the information that already occurs at Column 5, line 4 to Column 5, line 66 and from Column 7, line 5 to Column 7, line 11.

Column 53,
Line 66, "(IA)" should read as -- (IIA) --.

Column 56,
Lines 13-14, "[(2-morpholinoethyloxy)" should read as -- [4-(2-morpholinoethyloxy) --.

Signed and Sealed this

Fourteenth Day of August, 2001

Attest:

NICHOLAS P. GODICI
Attesting Officer    Acting Director of the United States Patent and Trademark Office